(12) United States Patent
Rocco et al.

(10) Patent No.: US 8,227,225 B2
(45) Date of Patent: *Jul. 24, 2012

(54) PLASTICIZED MYCELIUM COMPOSITE AND METHOD

(75) Inventors: Charles Alan Rocco, Milford, MI (US); Raymond Edward Kalisz, Livonia, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 84 days.

This patent is subject to a terminal disclaimer.

(21) Appl. No.: 12/797,384

(22) Filed: Jun. 9, 2010

(65) Prior Publication Data

US 2011/0269209 A1 Nov. 3, 2011

(51) Int. Cl.
*C12N 11/08* (2006.01)
*C12N 1/14* (2006.01)
*B27N 5/00* (2006.01)
*B23B 9/02* (2006.01)

(52) U.S. Cl. .................... 435/180; 435/254.1; 428/35.6; 428/411.1

(58) Field of Classification Search ........................ None
See application file for complete search history.

(56) References Cited

U.S. PATENT DOCUMENTS

| | | | |
|---|---|---|---|
| 3,616,246 A | 10/1971 | Cherry | |
| 3,892,905 A | 7/1975 | Albert | |
| 4,067,821 A | 1/1978 | Votápek et al. | |
| 4,073,956 A | 2/1978 | Yates | |
| 4,121,599 A | 10/1978 | Newton et al. | |
| 4,149,936 A | 4/1979 | Messing et al. | |
| 4,152,868 A | 5/1979 | Lincoln | |
| 4,153,510 A | 5/1979 | Messing et al. | |
| 4,321,327 A | 3/1982 | Chen et al. | |
| 4,378,378 A * | 3/1983 | Pell | 426/104 |
| 4,427,775 A | 1/1984 | Chen et al. | |
| 4,539,036 A | 9/1985 | Naschberger | |
| 4,735,218 A | 4/1988 | Akiko et al. | |
| 5,071,747 A | 12/1991 | Hough et al. | |
| 5,074,959 A * | 12/1991 | Yamanaka et al. | 162/9 |
| 5,352,709 A | 10/1994 | Tarrant et al. | |
| 5,620,498 A | 4/1997 | Ebert et al. | |
| 5,779,960 A | 7/1998 | Berlowitz-Tarrant et al. | |
| 5,786,188 A | 7/1998 | Lamar et al. | |
| 5,854,056 A | 12/1998 | Dschida | |
| 6,423,337 B1 | 7/2002 | Edebo | |
| 6,488,997 B1 | 12/2002 | Tong | |
| 7,556,946 B2 | 7/2009 | Versali et al. | |
| 2008/0145577 A1 | 6/2008 | Bayer et al. | |
| 2009/0307969 A1 | 12/2009 | Bayer et al. | |

FOREIGN PATENT DOCUMENTS

| | | |
|---|---|---|
| GB | 2188135 | 9/1987 |
| WO | WO 8702704 | 5/1987 |

OTHER PUBLICATIONS

Stamets, Paul, "Mycelium Running: How Mushrooms Can Help Save the World", pp. 1-5, 10-18, and 23-24, Crown Publishing Group, New York, 2005.

* cited by examiner

*Primary Examiner* — David Naff
(74) *Attorney, Agent, or Firm* — Gregory P. Brown; Price Heneveld LLP

(57) ABSTRACT

A method of making a plasticized mycelium structure, including dissolving a soluble polymer in a liquid thereby forming a polymer solution of polymer particles. The polymer solution is combined with a fungal inoculum capable of growing hyphae in the presence of an aggregate. The resulting mixture is allowed to grow into a mycelium network. The mycelium network is made up of hyphae which bond with the polymer particles found in the polymer solution forming a structure substantially made up of mycelium that has a plasticizer homogenously distributed throughout the structure. The structure is cured to terminate mycelium growth.

8 Claims, 23 Drawing Sheets

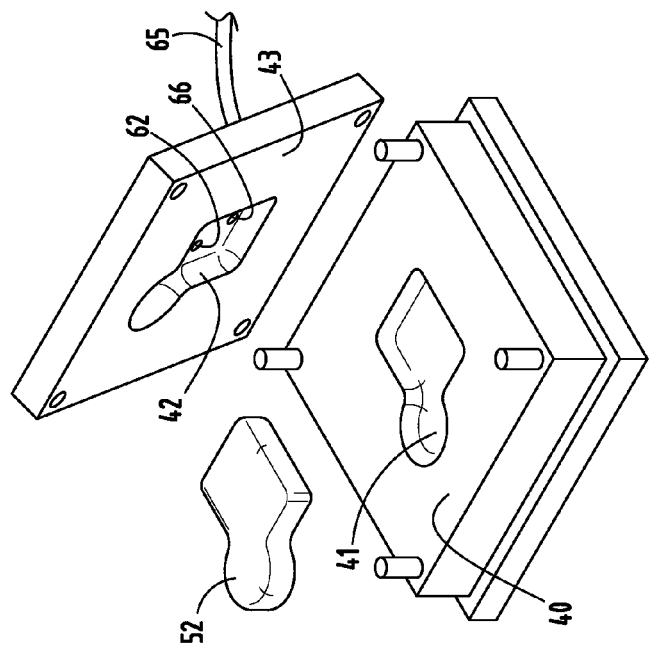
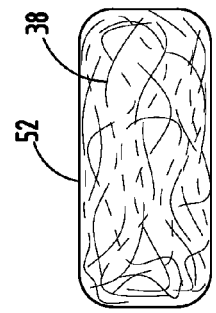
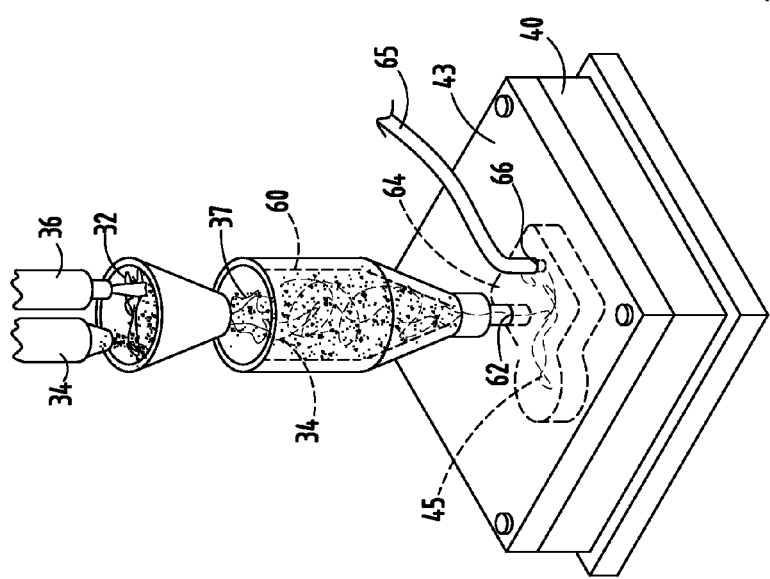
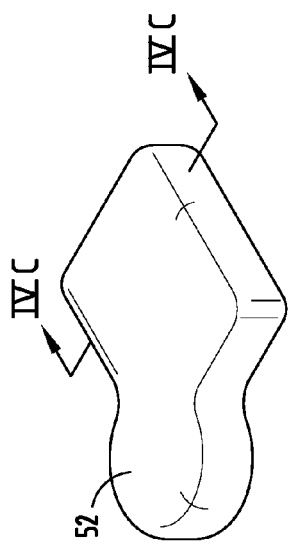
FIG. 4A
FIG. 4C
FIG. 4B
FIG. 4

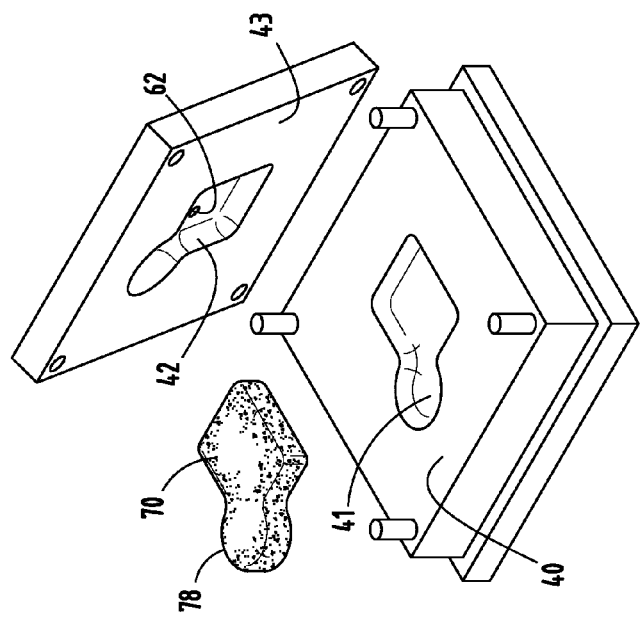
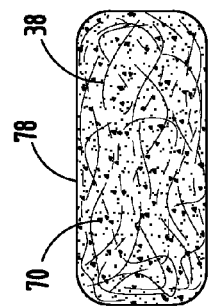
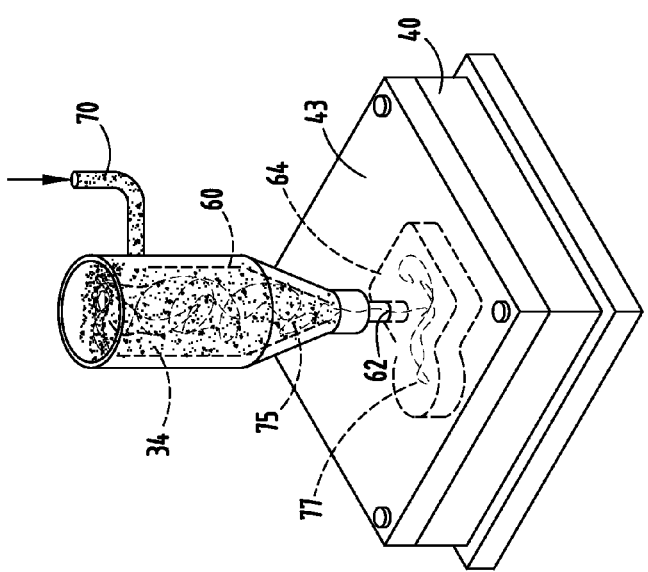
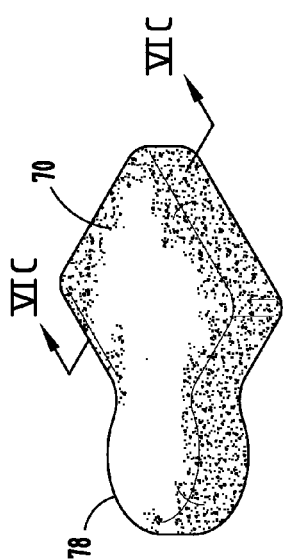

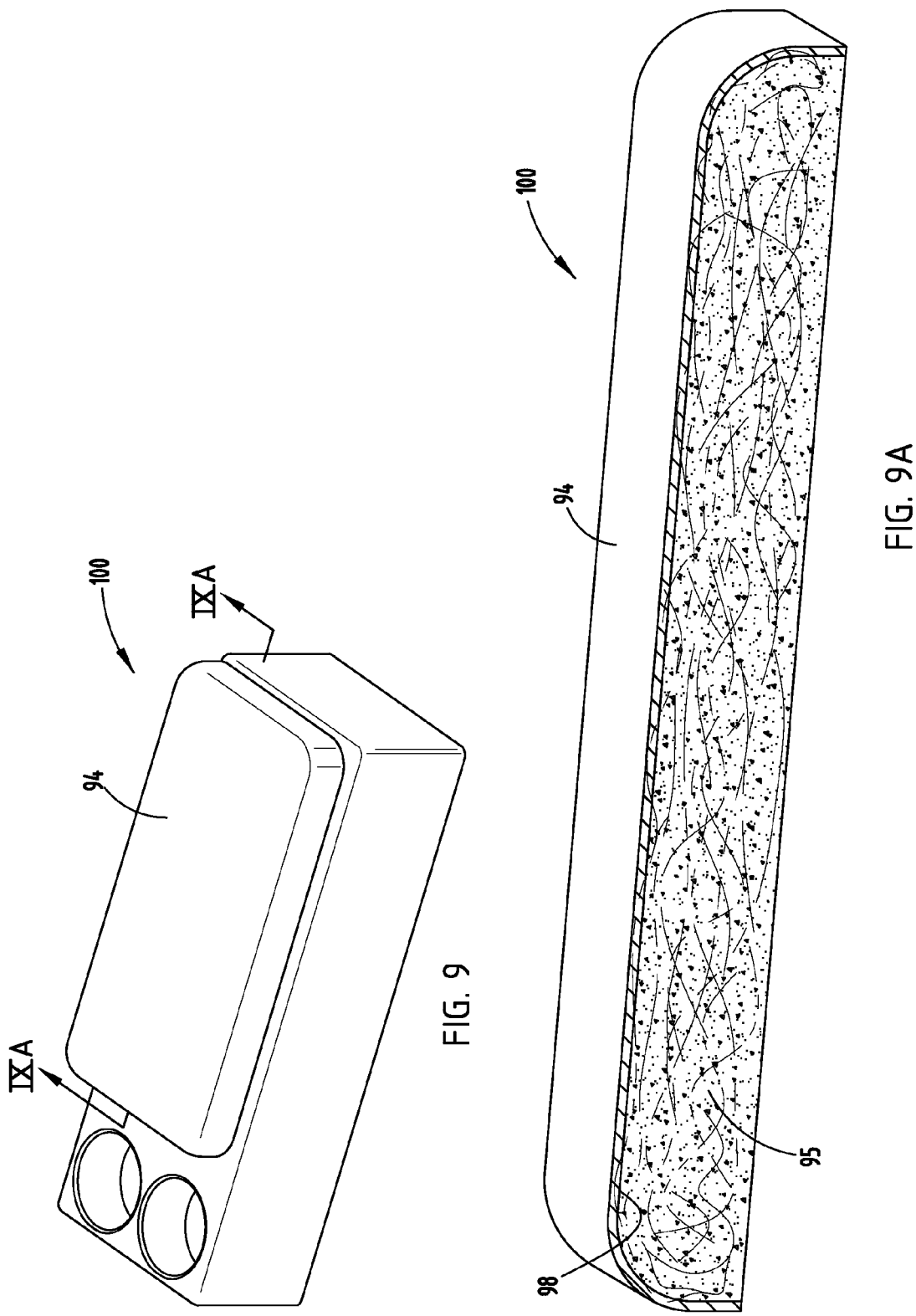

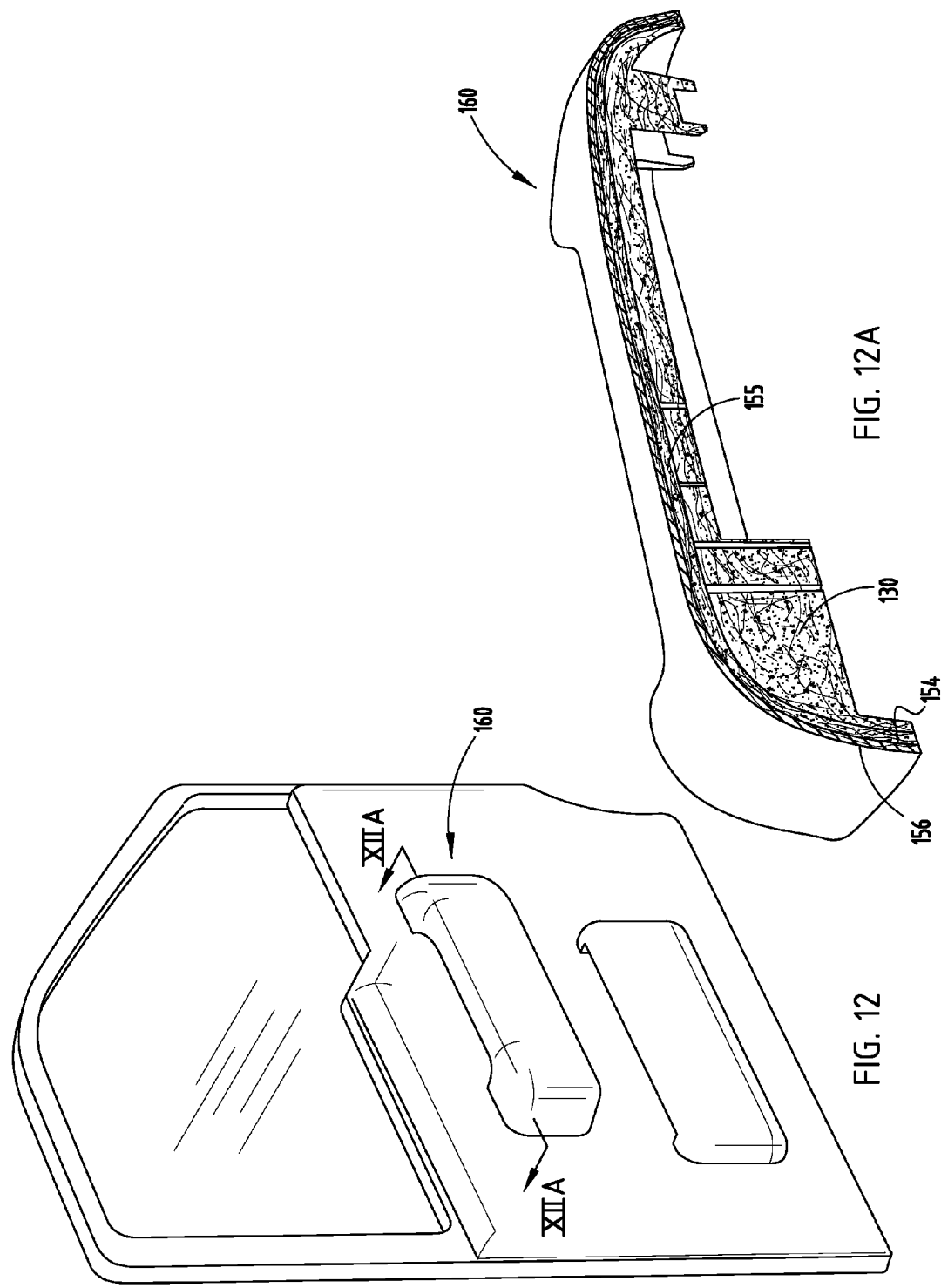

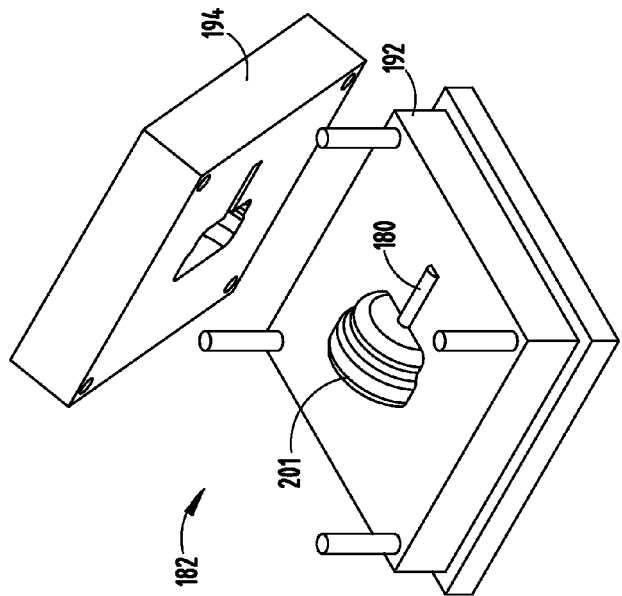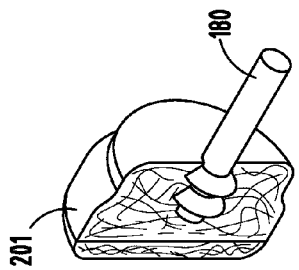
FIG. 14A
FIG. 14C
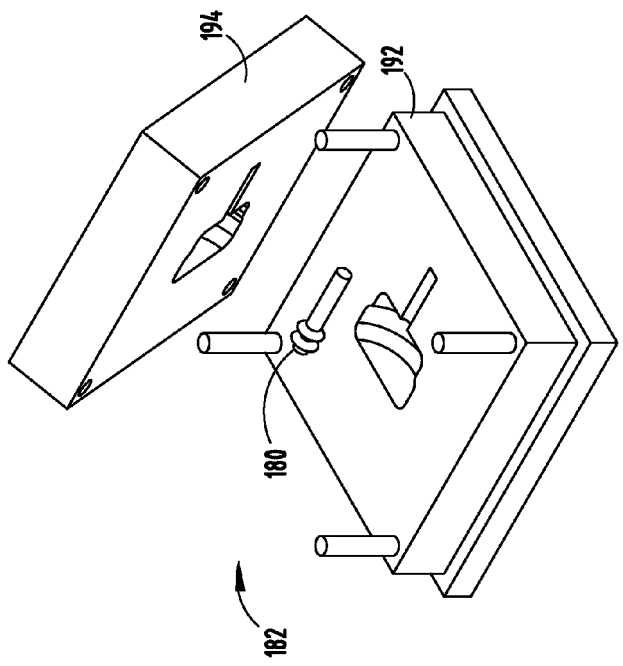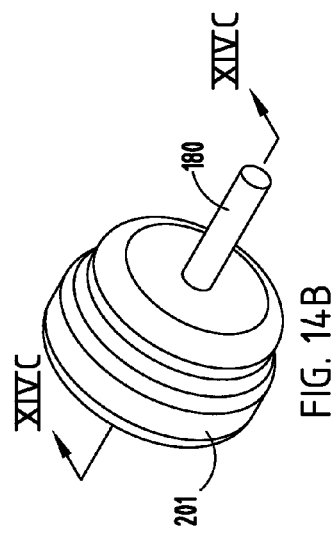
FIG. 14
FIG. 14B

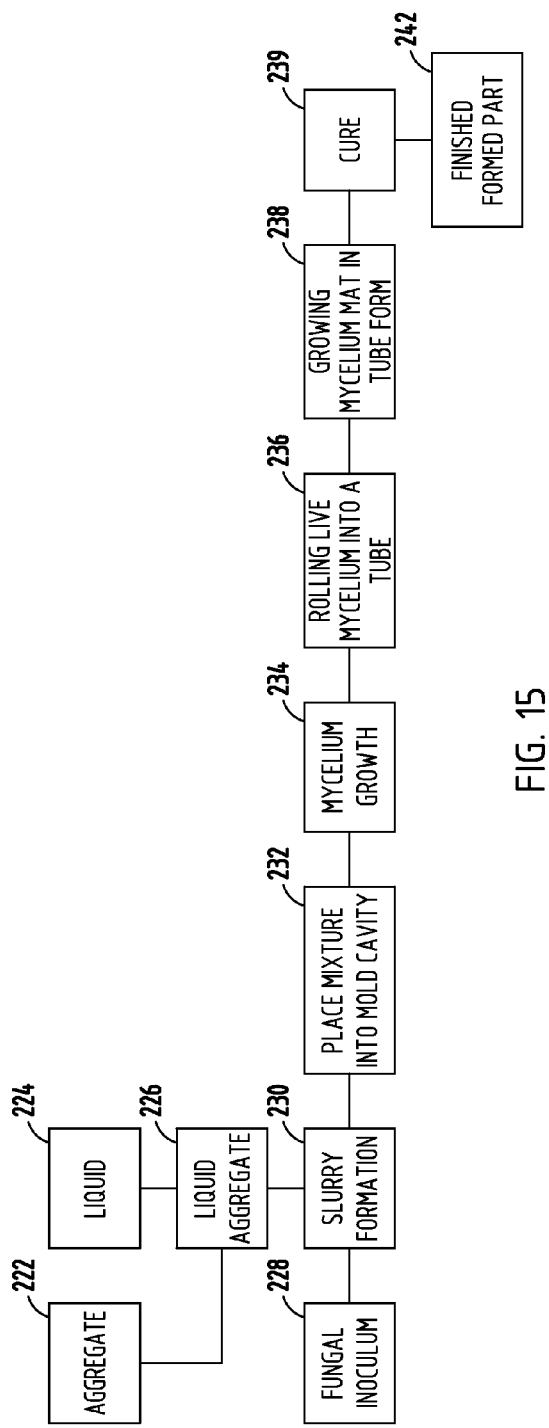
FIG. 15
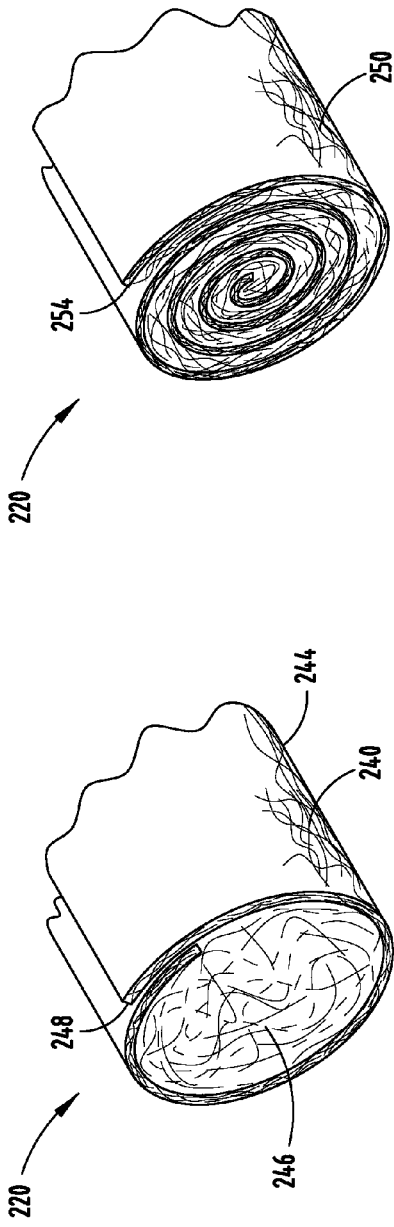
FIG. 15B
FIG. 15A

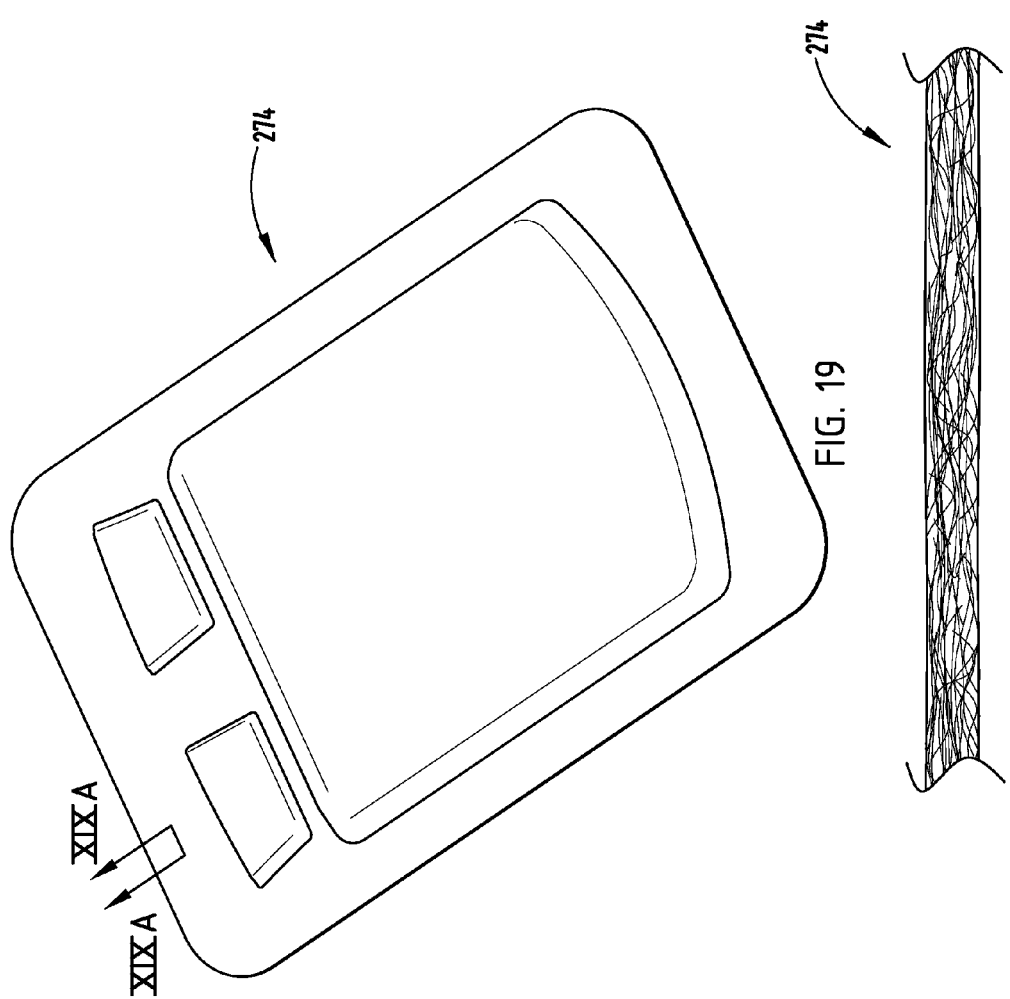

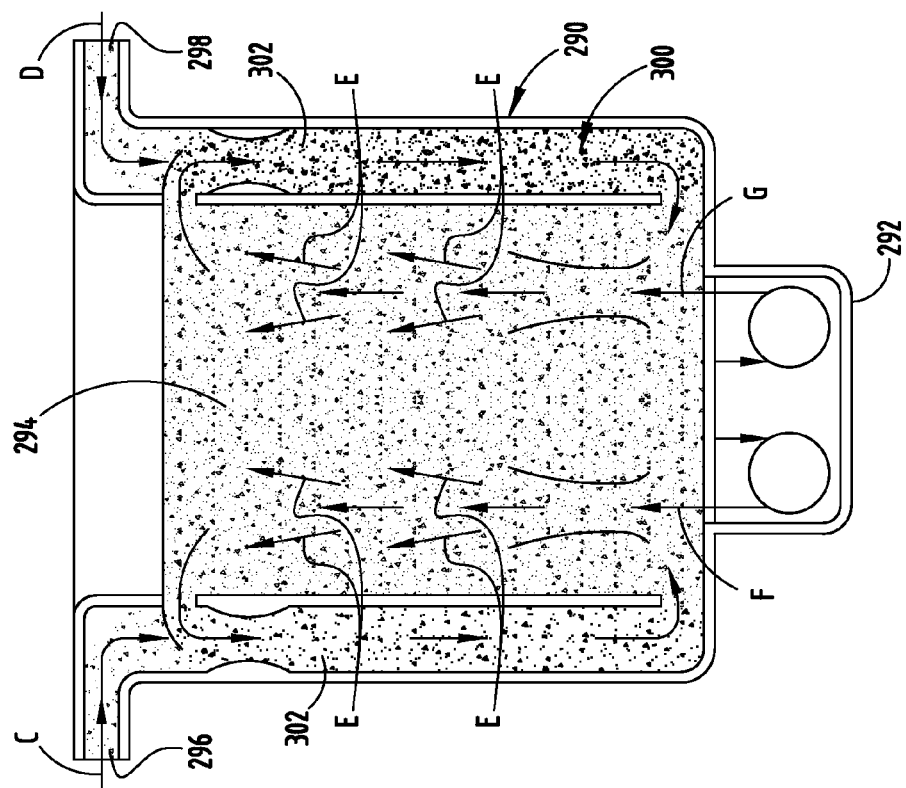
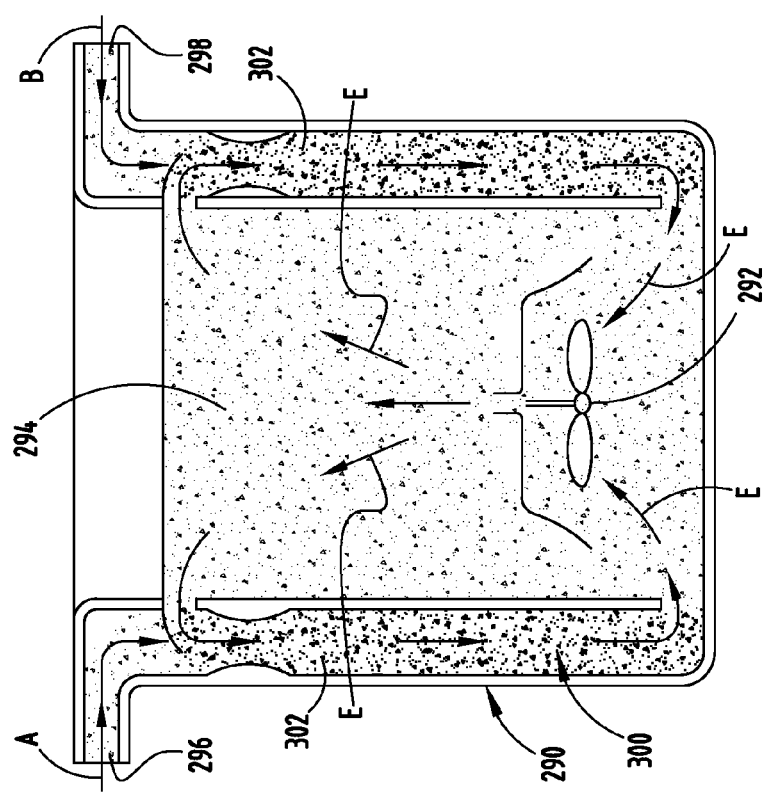

PLASTICIZED MYCELIUM COMPOSITE AND METHOD

FIELD OF THE INVENTION

The present invention generally relates to a mycelium composite and a method of making the same, and more particularly to a method of making composite parts that include a mycelium component and a plasticizer.

BACKGROUND OF THE INVENTION

Plastics and plastic foams have been widely used in a multitude of industrial and consumer applications. Specifically, urethane plastics, foams and elastomers, as well as other like petroleum-based products have been used in the automobile industry, for example, for outfitting vehicle interiors. Given the non-biodegradable nature of these materials, as well as the limited availability and time-intensive process for renewing these resources, the interest in biodegradable or "green" components has steadily increased. The present invention relates to a "green" raw material that can be used in the production of composite materials for industries that currently employ petroleum-based and other like plastics and foams.

SUMMARY OF THE INVENTION

One aspect of the present invention includes a method of making a plasticized structure, including dissolving a soluble polymer in a liquid thereby forming a polymer solution of polymer particles. The polymer solution is combined with a fungal inoculum capable of growing hyphae in the presence of an aggregate. The resulting mixture is allowed to grow into a mycelium network. The mycelium network is made up of hyphae which bond with the polymer particles found in the polymer solution. This forms a structure substantially made up of mycelium that has a plasticizer homogenously distributed throughout the structure. The structure is cured to terminate mycelium growth.

Another aspect of the present invention includes a method of making a plasticized structure, including providing a mixture of a fungal inoculum and an aggregate and allowing the mycelium to enter the growth cycle and grow into a mycelium structure. The mycelium stricter is treated with a plasticizer during the growth cycle and the hyphae that grow during the growth cycle bond with the plasticizer to form a composite structure. The composite structure is then cured to end the growing cycle.

Yet another aspect of the present invention includes a vehicle part having a body portion substantially comprised of mycelium formed in a closed mold. The part has a plasticizer homogenously distributed throughout the body portion.

These and other aspects, objects, and features of the present invention will be understood and appreciated by those skilled in the art upon studying the following specification, claims, and appended drawings.

BRIEF DESCRIPTION OF THE DRAWINGS

FIG. 4 is a top perspective view of one embodiment of an injection molding device for making a molded mycelium component;

FIG. 4A is a top perspective view of the injection molding device of FIG. 4 with the second mold cavity separated from the first mold cavity;

FIG. 4B is a top perspective view of one embodiment of a molded mycelium component;

FIG. 4C is a cross-sectional view of the molded mycelium component taken at line IVC-IVC;

FIG. 6 is a top perspective view of another embodiment of an injection molding device for making a molded composite mycelium component;

FIG. 6A is a top perspective view of the device of FIG. 6 with the second mold cavity separated from the first mold cavity;

FIG. 6B is a top perspective view of a composite mycelium component;

FIG. 6C is a cross-sectional view of the molded composite mycelium component taken at line VIC-VIC;

FIG. 9 is a top perspective view of one embodiment of the console armrest IX of FIG. 2 incorporating a mycelium component;

FIG. 9A is a side elevational cross-sectional view of the console armrest of FIG. 9 taken at line IXA-IXA;

FIG. 12 is a top perspective view of one embodiment of the door armrest XII of FIG. 2 incorporating a dual mycelium component;

FIG. 12A is an enlarged view of the door armrest of FIG. 12 taken at line XIIA-XIIA;

FIG. 14 is a top perspective view of one embodiment of a molding device for connecting an object to a mycelium structure;

FIG. 14A is a top perspective view of the molding device of FIG. 14 after making a mycelium component with an object disposed therein;

FIG. 14B is a top perspective view of the mycelium component of FIG. 14A with an object disposed therein;

FIG. 14C is a top perspective cross-sectional view of the mycelium component of FIG. 14B taken at line XIVC-XIVC;

FIG. 15 is a flow chart illustrating one embodiment of a method of making a tubular mycelium component;

FIG. 15A is a top perspective view of an end of a tubular mycelium component;

FIG. 15B is a top cross-sectional view of another embodiment of a tubular mycelium component;

FIG. 19 is a top perspective view of one embodiment of the headliner XIX of FIG. 2 incorporating a mycelium component;

FIG. 19A is a side cross-sectional view taken at line XIXA-XIXA;

FIG. 21 is a side cross-sectional elevational view of one embodiment of an agitating vessel used in making a foamed mycelium component; and FIG. 22 is a side cross-sectional view of another agitating vessel.

DETAILED DESCRIPTION OF EMBODIMENTS

Figure 2:
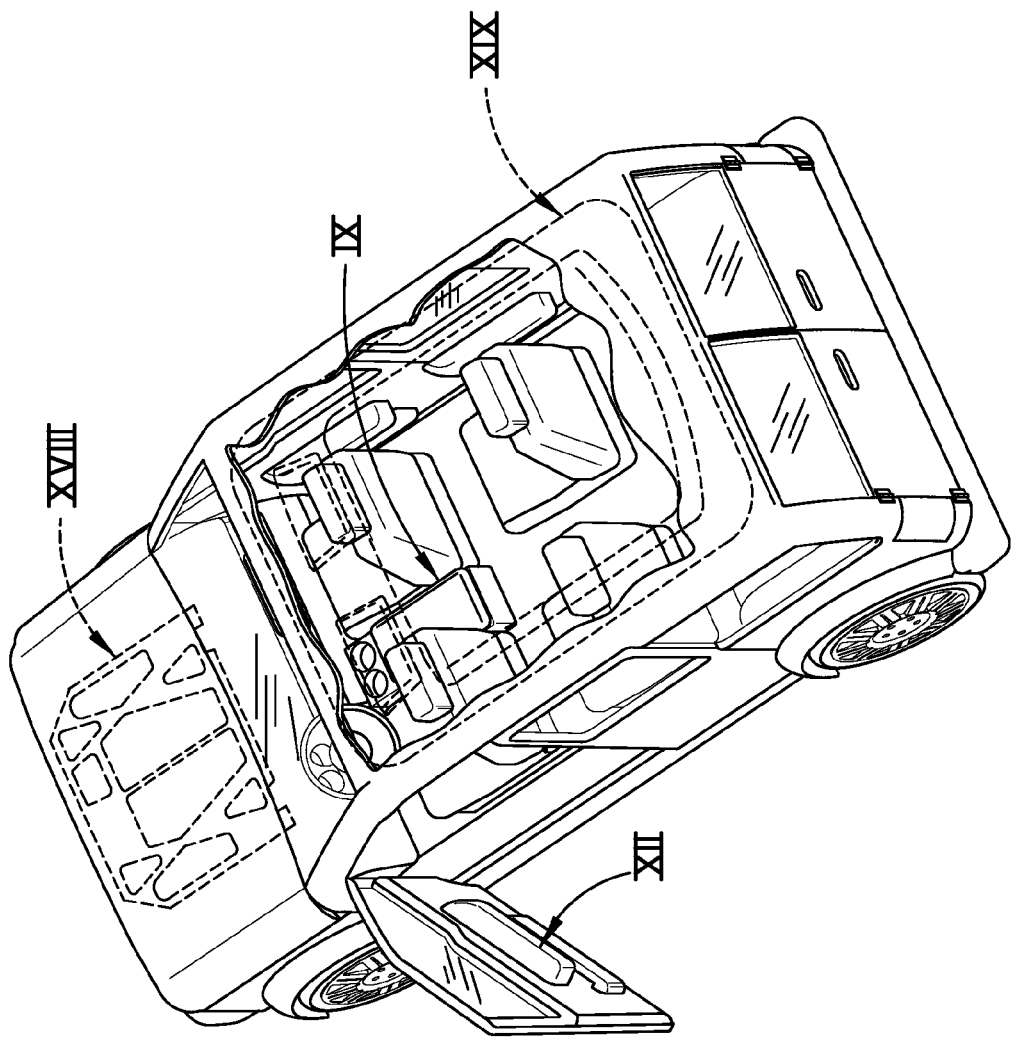
FIG. 2 is a top perspective view of a vehicle incorporating several embodiments of a mycelium component of the present invention.

For purposes of description herein, the terms "upper," "lower," "right," "left," "rear," "front," "vertical," "horizontal," and derivatives thereof shall relate to the invention as oriented in FIG. 2. However, it is to be understood that the invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
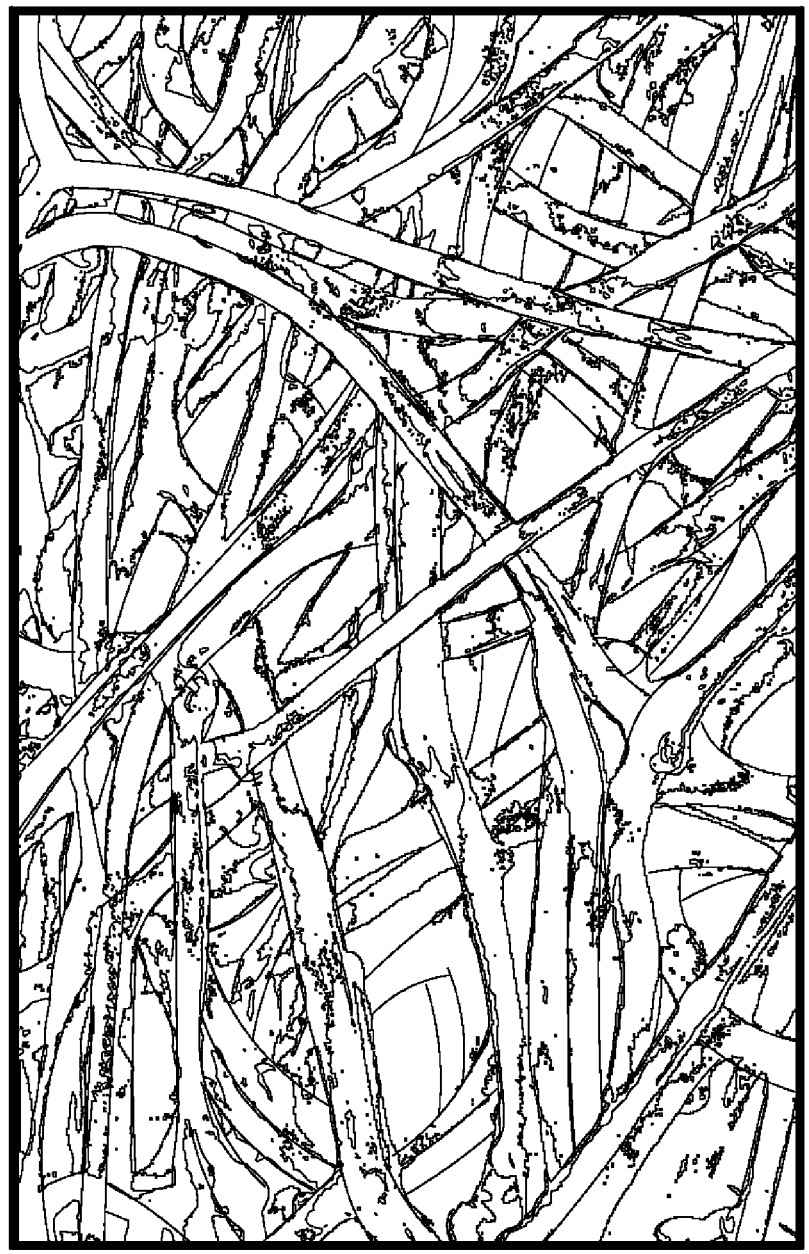
FIG. 1 is a magnified view of a living mycelium structure.

Fungus is an abundant fast-growing member of a large group of eukaryotic organisms, which includes mushrooms. Collectively, fungi are classified in their own kingdom, separate from plants and animals. The Fungi Kingdom has been estimated to contain about 1.5 million species. Certain species of fungi have demonstrated growing capabilities along with pronounced physical properties making them a suitable substitute for some components found in a variety of present day plastics and foams. Most species of fungi have a well developed mycelium component through which the fungus communicates with its environment, and it is this fungal component that has vast potential for incorporation into parts for a variety of industries. Mycelium, as shown in FIG. 1, is made up of masses of hyphae, which are filamentous, tubular, thread-like structures (which can be anywhere from about 2 to about 10 µm in diameter) that can grow to be several centimeters in length. Hyphae generally grow at the tips of individual hypha. The tip of a hypha is known as the apex and each apex generally contains a set of aggregated vessels, which are cellular structures comprising proteins, lipids, and other such organic molecules. Through a process known as branching, hyphae typically grow and elongate, forming new tips along existing hyphae apices, or a growing hypha can bifurcate at its apex, resulting in two parallel growing hyphae. These are some ways in which fungi grow towards their food sources. Most filamentous fungi grow in a polar fashion, whereby the hyphae extend from their apices in one direction. Intercalary extension also occurs in some species, whereby hyphal compartments below the apex expand longitudinally. Volume expansion also occurs in certain species during the development of mushroom stipes and other large fungal organs. The extension of existing hyphae through polar apical growth, intercalary extension, volume extension, and bifurcation results in the development of a highly complex membrane of interweaving, continuously branching cell chains forming an interconnected mycelium network.

Mycelium is often referred to as the vegetative component of a fungus. Mycelium typically runs under the top few inches of soil with some species of fungi having mycelium components that can grow several inches in a day. A mycelium mat, a structure made up of several different mycelium networks, can cover thousands of acres. The network-like structure of mycelium is used to absorb nutrients from the environment for nourishment of the associated fungus. Specifically, the hyphae secrete enzymes, which contact potential food sources. These enzymes breakdown the complex polymeric structure of the food source into basic monomers which can be absorbed by the mycelium through diffusion or active transport and then be digested by the fungus.

The Fungi Kingdom is often compared to the Plant Kingdom, but the differences between these Kingdoms are notable. The eukaryotic cells of fungi have cell walls that contain glutens (such as $\beta$-1,3-glucan) and the biopolymer chitin. Unlike fungi, the cell walls of plants contain the polysaccharide cellulose. Fungi are the only organisms known to contain both of the structural molecules chitin and glucans in their cell walls. Chitin is a nitrogen-containing modified polysaccharide, which forms not only a principle component of fungi cell walls, but is also a principle component in arthropod exoskeletons, such as crustaceans, insects, and in the beaks of cephalopods like octopi and squids.

As depicted below, chitin has an acetyl amine group on each monomer as well as a hydroxyl group. Cellulose has two hydroxyl groups on each monomer, and it is the presence of the acetyl amine group in the chitin structure that allows for increased hydrogen bonding between chitin and adjacent polymers as compared to cellulose. The ability to form more hydrogen bonds gives a chitin polymer matrix increased tensile strength. Mycelium aggressively branches through subterranean landscapes, thereby coming into direct contact with a myriad of organisms that could infect or harm the associated fungus. Yet, mycelium flourishes in nature and is adequately protected by the formidable chitin molecules found in the fungi cell wall, even though the mycelium structure is only one cell wall thick.

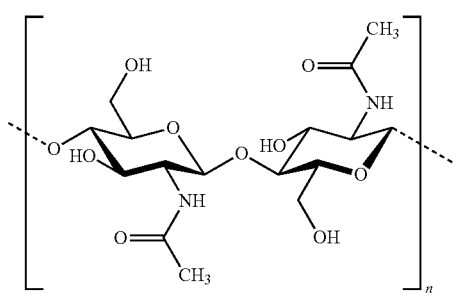

Chitin Chemical Structure

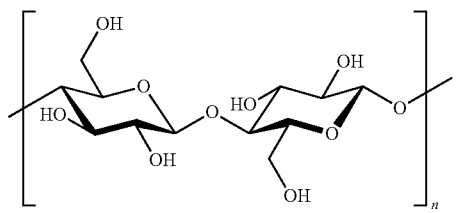

Cellulose Chemical Structure

Mycelium's ability to adapt, evolve, and flourish in a number of environments make it an ideal resource for growing either in a lab or in natural conditions for the cultivation of the resource for industrial applications. Fungi have a high degree of metabolic versatility that allows them to draw on a diverse range of potential food sources for growth. Simple compounds, such as nitrate, ammonia, acetate, and ethanol, can be metabolized by a fungus through its mycelium. Fungi species exhibiting growth qualities and structural properties suitable for the embodiments disclosed in the present application include, but are not limited to, *Pleurotus djamor*, *Pleurotus eryngii*, *Pleurotus ostreatus*, *Pleurotus ostreatus* var. *columbines*, *Grifola frondosa*, *Ganoderma lucidum*, *Ganoderma oregonense*, *Lentinula edodes*, *Agrocybe aegerita*, or *Coprinus Comatus*. As noted above, the Fungi Kingdom is comprised of millions of species, and a multitude of these species would be suitable for use in the present invention.

Fungi's rapid growth rate is partially attributable to the fact that fungi can reproduce both sexually and asexually. Both forms of reproduction can produce spores. Asexual reproduction can occur through the production of vegetative spores known as conidia. Conidia are produced on the ends of specialized hyphae called conidiophores. Mycelium fragmentation is another form of asexual reproduction. Sexual reproduction most often occurs when compatible fungi combine their mycelia by fusing their hyphae together into an interconnected network often referred to as a mycelial mat. This fusion of hyphae is known as plasmogamy and it forms a heterokaryotic structure, which produces dikaryotic hyphae. Fungi's prolific reproduction systems and metabolic versatility make fungi a fast-growing and readily abundant resource.

Mycelium growth can be recreated by placing a fungal inoculum into a growing medium. A fungal inoculum is made up of a fungal propagule, which can be any vegetative, sexual, or asexual structure of a fungus that is capable of growing a new fungal colony. One skilled in the art will recognize that there are several ways to grow and prepare particular fungal strains and strain cultures are themselves commercially available from sources such as www.fungi.com. Fragmentation of mycelium is a way to cultivate a suitable propagule. In order to grow a mycelium network, the fungal inoculum should be placed in contact with a nutrient source which the fungus can digest. A suitable nutrient source can be in the form of an aggregate and can contain several different nutrients, depending on the particular fungus sought to be grown. Such nutrients include fibrous materials, such as agricultural and wood by-products. Specifically, the following exemplary nutrient sources can be used to feed a fungal inoculum for the growing of mycelium: bamboo, brewery waste, cacao shells, cacti, coconut fiber, straws, fabrics, garden waste, hair, hemp, leaves manure, nut casings, seed hulls, rice, oils, paper products, textiles, and by-products of corn, cotton, coffee beans, soybeans, rice, straw, sugarcane, and tobacco. Other nutrient sources will be recognized by one skilled in the art.

A nutrient source containing lignin makes for an excellent source of nutrients as well as provides the grown mycelium with desirable characteristic for forming a composite structure. Lignin is a biopolymer generally found in the cell walls of plants. Lignin is known for providing plants with structural support and is particularly known for its strengthening of wood. Lignin facilities plant support and strength by its natural ability to crosslink with different plant polysaccharides and cell wall components. It is the crosslinking ability of lignin that provides excellent mechanical strength. Fungi are able to digest lignin through the use of enzymes known as ligninases which allow the fungi to metabolize the lignin structures. Through this process, the lignin becomes part of the mycelium structure and on a molecular level, is able bring its crosslinking abilities and strength to the mycelium network. Wood by-products are a good nutrient source having lignin for use in the present invention.

As noted above, a fungal inoculum needs a nutrient source to grow. One way to get an inoculum in contact with a nutrient source is to prepare the inoculum by blending the fungal propagule into smaller pieces suitable for incorporation into a liquid or solvent. This creates an inoculum solution which has an even distribution of the propagule throughout. The inoculum solution can be introduced into a liquid aggregate to form a wet slurry. Once in contact, the wet slurry is incubated in proper atmospheric conditions such that the inoculum can rapidly grow, feeding off the nutrients of the aggregate and forming a new fungal colony of fungal mycelia. Incubation under proper atmospheric conditions can provide a cultivatable product in less than two weeks. Proper atmospheric conditions generally include a damp dark location that is oxygen rich and having a temperature between 55-90 degrees Fahrenheit. The humidity is generally kept high in a range from about 20-100 percent. If reduced fruiting is desired, the temperature is generally kept above 70 degrees Fahrenheit. The fungal inoculum or the aggregate can be combined with the other in dry particle form, or in solution.

Referring to FIG. 2, the reference numeral 20 generally designates a vehicle incorporating mycelium-based components. The mycelium-based components may be implemented in a variety of parts, including, but not limited to, door bolsters, door armrests, console armrests, and energy absorbers, such as bumpers, headliners, dashes, seats, floors, heat shields, sound insulators, etc. The mycelium-based components offer a light-weight, cost-effective biodegradable alternative to traditional non-biodegradable vehicle parts. The processes by which the mycelium-based components can be constructed are outlined in greater detail below. The mycelium-based components can be used in a wide variety of industries and applications. It will be understood that any of the processes discussed below could be used to construct nearly any of the parts discussed below, and that the parts discussed are to serve as examples only.

Figure 3:
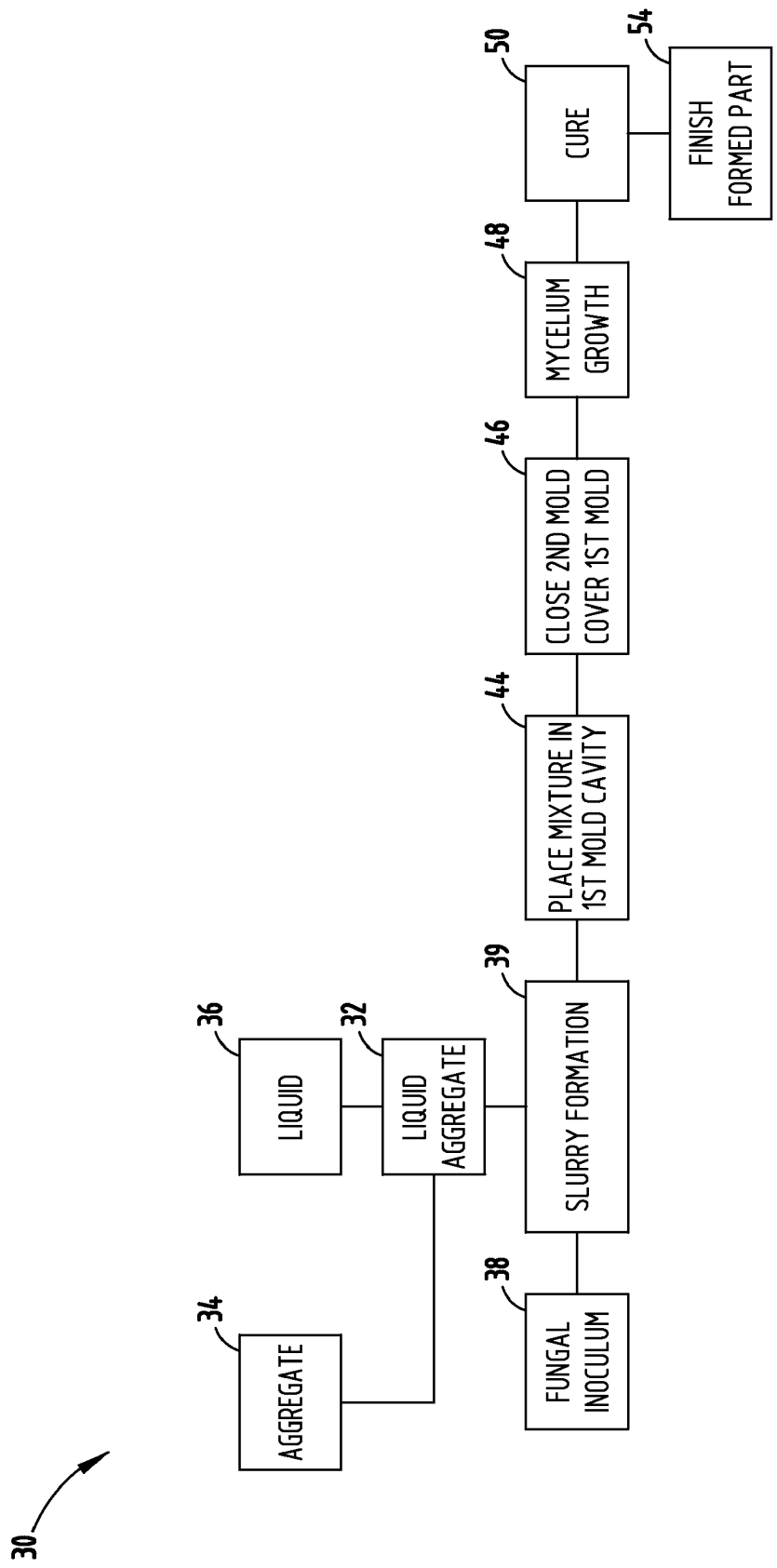
FIG. 3 is a flow chart illustrating one embodiment of a method of making a mycelium component.

Referring to FIGS. 3 and 4-4C, one method of making a molded part 30 includes forming a liquid aggregate 32 from a mixture of finely ground aggregate 34 and a liquid 36. A fungal inoculum 38 and the liquid aggregate 32 are mixed in step 39 to form a slurry 37 and are inserted into a first mold 40 having a first mold cavity 41 (step 44). The first mold cavity 41 is then sealed against a second complementary mold cavity 42 located in a second mold 43 (step 46). Live mycelium 45 is grown from the fungal inoculum 38 to fill the first and second mold cavities 41, 42 (step 48). The live mycelium 45 is cured by heating (step 50) to terminate further growth of the fungal inoculum 38, thereby developing a formed part 52 (step 54).

Referring again to FIGS. 4-4C, the formed part 52 is generally formed by an injection molding device that utilizes an injector 60 that injects a mix of predetermined liquid aggregate 32 and the fungal inoculum 38 through an internal injection port 62. The aggregate may be any of a number of aggregates as listed above. The liquid aggregate 32 provides the nutrient source needed by the fungal inoculum 38 to grow and may also act as a binder dispersed throughout the slurry 37 as it grows into the live mycelium 45. In this application, the ground aggregate 34 is contemplated to be of a size less than or equal to two inches. The liquid 36 is then mixed with the finely ground aggregate 34 to create a liquid aggregate 32. It is contemplated that the viscosity of the liquid aggregate 32 may range from that of water to that of a very thick sludge. The liquid 36 may be an aqueous or oil-based solution. The consistency of the liquid aggregate 32 will change depending on the final desired qualities of the formed part 52. The liquid aggregate 32 is then mixed with the fungal inoculum 38 to form a relatively homogenous slurry 37. After the slurry 37 has been thoroughly mixed, the slurry 37 is ready for injection molding.

To begin the injection molding process, the slurry 37 is placed into the first mold cavity 41 that is shaped to form the part desired. It is contemplated that the first mold cavity 41 may include any of a variety of constructions, including that of a clam shell injection mold, or hydraulic press injection mold. After the slurry 37 has been placed into the first mold cavity 41, the second complementary mold cavity 42 is sealed against the first mold cavity 41 to form a closed growth cavity 64. The closed growth cavity 64 forms an incubator-like recess in which mycelium 45 grows from the slurry 37. More specifically, the fungal inoculum 38 begins to feed on the nutrient source present in the slurry 37. The nutrient source is primarily lignin. After a predetermined length of time, the mycelium 45 grows into the closed growth cavity 64, substantially filling all the voids and corners of the closed growth cavity 64. After a predetermined length of time, the mycelium 45 is cured. In one embodiment, the closed growth cavity 64 is heated to approximately 125 degrees Fahrenheit for a period of one to 15 days to terminate further growth of the mycelium 45. The resulting formed part 52 is substantially comprised of mycelium. The formed part 52 is removed from the first and second mold cavities 41, 42 and may be finished to provide a smooth outside appearance and installed in a vehicle (FIG. 2). It will be understood that the curing process can be accomplished by raising or lowering the temperature in the mold cavities 41, 42. Alternatively, oxygen may be removed or carbon dioxide added, an electrical current applied, or a curing chemical applied. Other possible curing methods are also contemplated.

In another embodiment, after the first mold cavity 41 and second complementary mold cavity 42 are sealed to form the closed growth cavity 64, pressure may be applied from a pressure hose 65 to the closed growth cavity 64 during growth of the mycelium 45. The pressure hose 65 includes a pressure port 66 in fluid communication with the growth cavity 64. As will be understood by one having ordinary skill in the art, the pressure that is applied to the closed growth cavity 64 will not be so high as to terminate the growth of the mycelium 45 during the mycelium growth process. Rather, it is contemplated that the introduction of pressurization may assist in forcing oxygen or other preferred gas into the slurry 37 and aid in the growth process.

Figure 5:
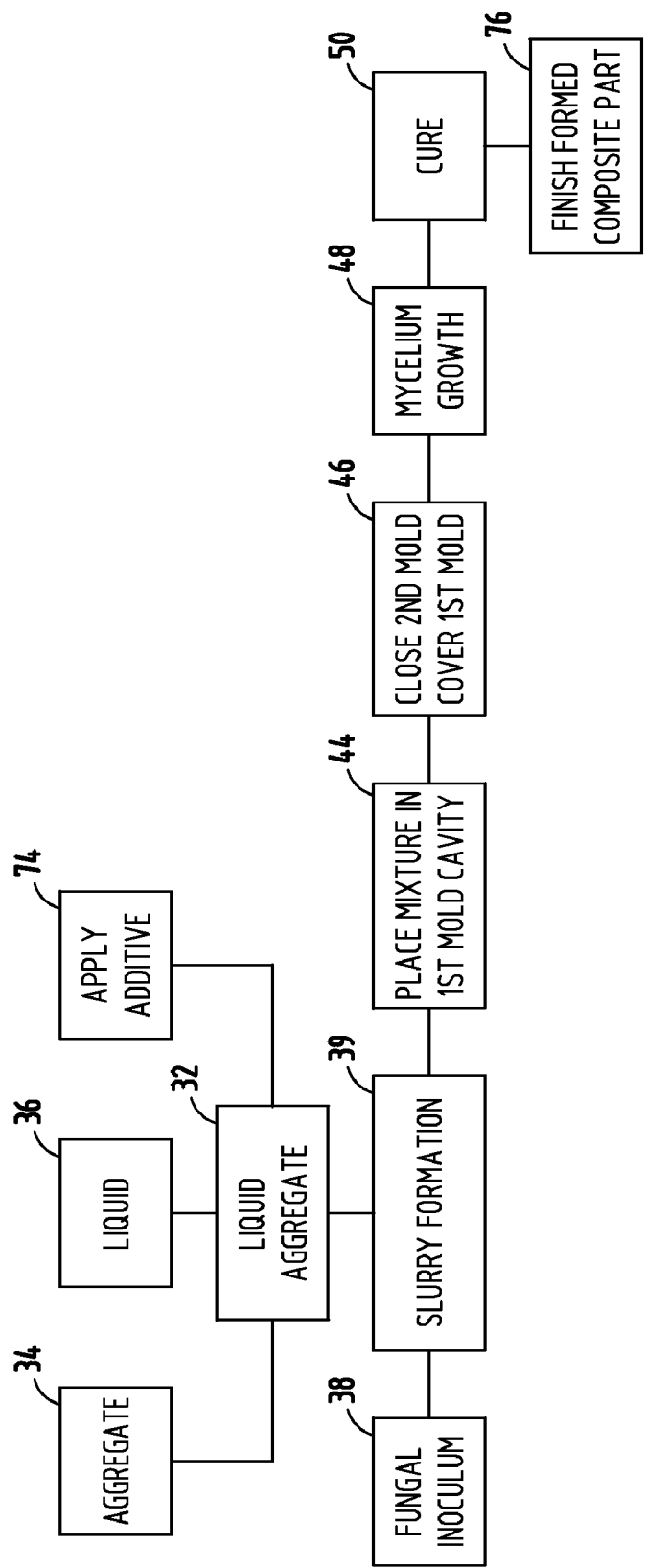
FIG. 5 is a flow chart illustrating another embodiment of a method of making a molded mycelium component.

In the method illustrated in FIGS. 5 and 6-6C, a particulate additive 70, such as a nanoparticle, is incorporated into the liquid aggregate 32 prior to or during mixing of the liquid aggregate 32 with the fungal inoculum 38 (step 74) to form a slurry 75. The slurry 75 grows into live mycelium 77. As a result, during the mycelium growth cycle, a nanoparticle/mycelium composite material 78 is formed (step 76) having different physical, chemical, and electrical characteristics than if the additive 70 was not present. The nanoparticles 70 are mixed with the slurry 75, such that the resulting nanoparticle/mycelium composite material 78 has nanoparticles 70 that are evenly distributed throughout the matrix of the mixture (FIG. 2). It is contemplated that the nanoparticles 70 may increase or decrease various physical or chemical properties of the mixture. Specifically, the nanoparticles 70 may increase or decrease the electrical conductivity, resiliency, deflective capabilities, durability, rigidity, etc. Accordingly, the addition of nanoparticles 70 can result in thinner wall sections in the composite formed part 52 than can be formed with pure mycelium 45. Parts made with nanoparticles 70 effectively stiffen the mycelium formed part 52, such that the formed part 52 has a higher flex modulus and a higher impact strength. Some such nanoparticles 70 include nanoclay and nanocarbon fiber. It is also contemplated that the addition of metallic nanoparticles 70 may increase the conductivity of electricity through the formed part 52. Alternatively, it is contemplated that the additive could be a variety of different additives or a combination of several additives. A plasticizer that aids in forming a rigid formed part after termination of the mycelium growth may also be utilized.

One example of a suitable plasticizer is a soluble polymer that is incorporated into the slurry. Water soluble plastic films are soluble polymers which have physical properties that are similar to that of polymers found in blown plastic films. Water soluble plastic films can dissolve entirely when placed in contact with a sufficient amount of liquid. Some water soluble films also have the ability to reconstitute after they have been dissolved when the liquid is evaporated. Currently, water soluble polymers have various uses in a range of industries from water-soluble packaging, barrier films, graphics film, medical supplies, and others.

Figure 5A:
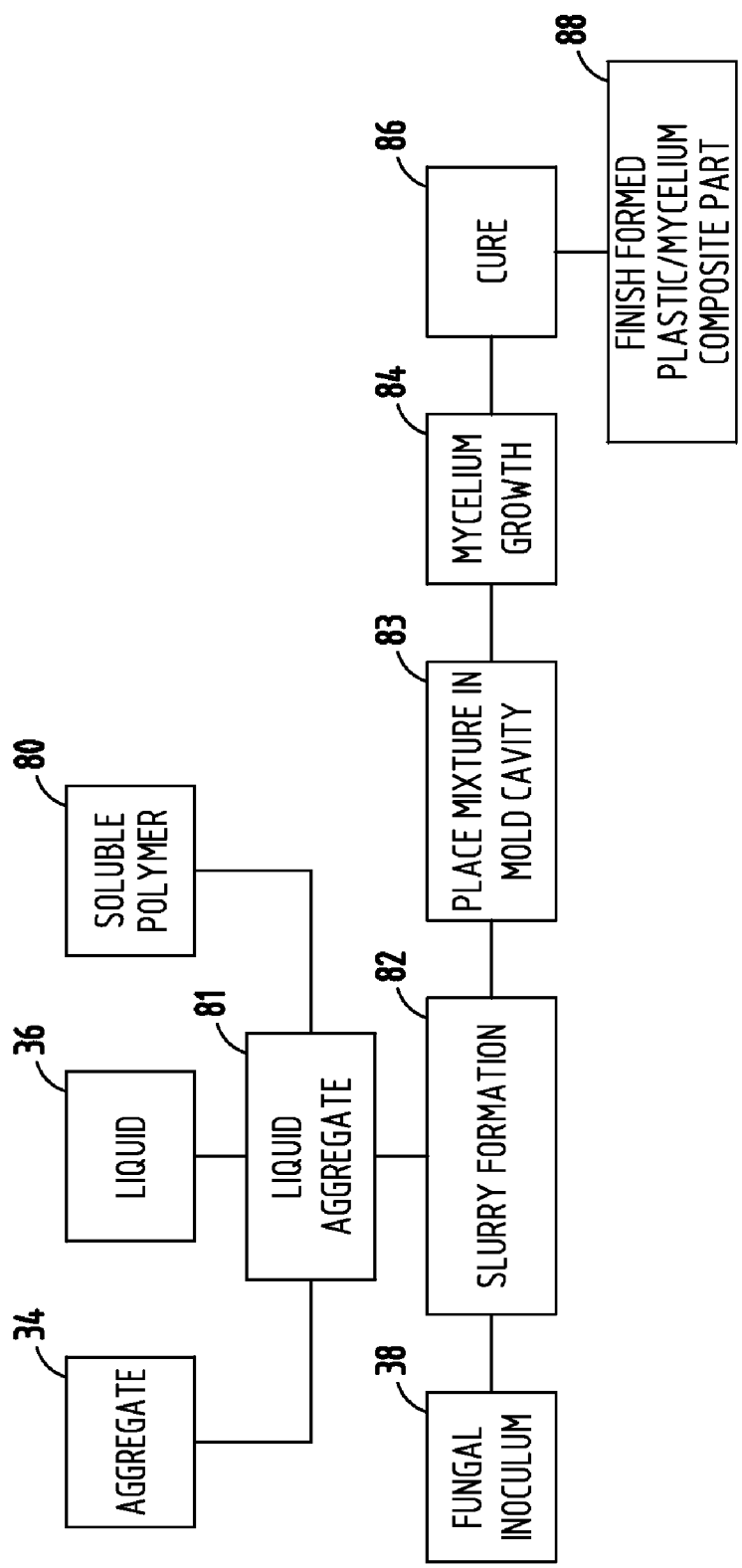
FIG. 5A is a flow chart of yet another embodiment of a method of making a molded mycelium component.
Figure 7:
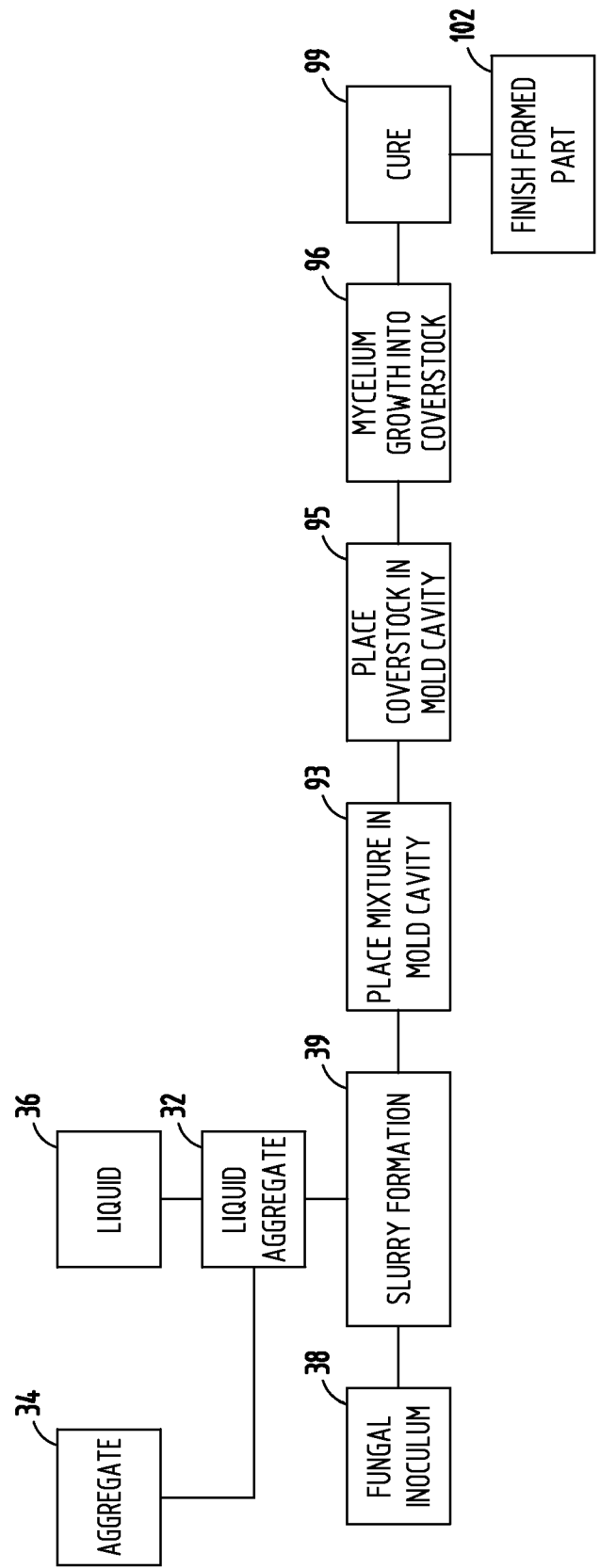
FIG. 7 is a flow chart of yet another embodiment of a method of making a mycelium component.
Figure 8A:
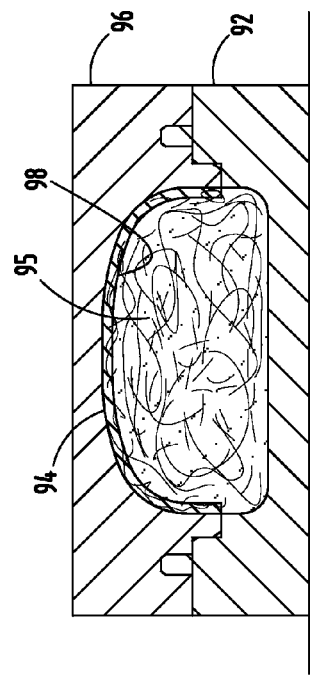
FIG. 8A is a side elevational cross-sectional view of one embodiment of a molding device for molding mycelium components.
Figure 8B:
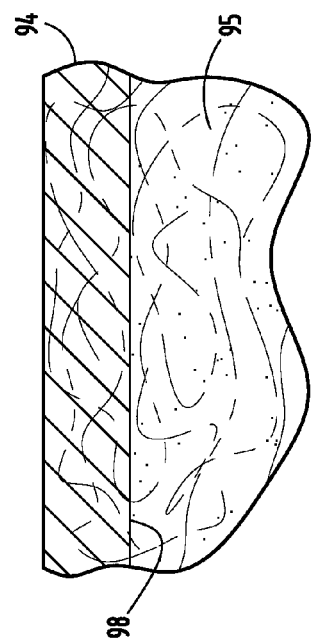
FIG. 8B is a side elevational cross-sectional view of the molding device of FIG. 8A with the mold cavities closed.
Figure 8C:
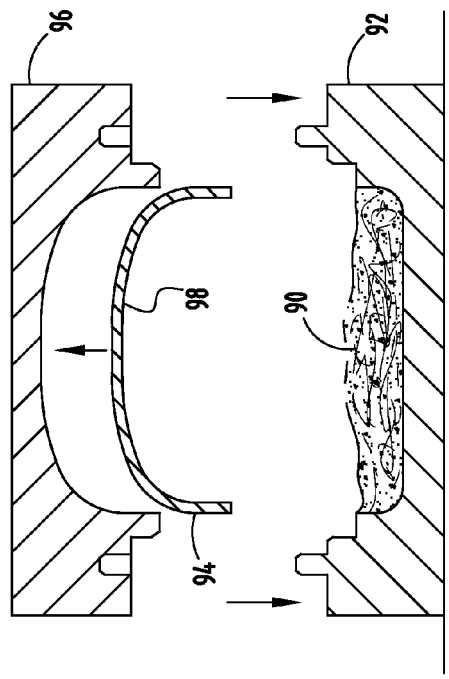
FIG. 8C is a side elevational cross-sectional view of the molding device of FIG. 8A with the mold cavities open.
Figure 8D:
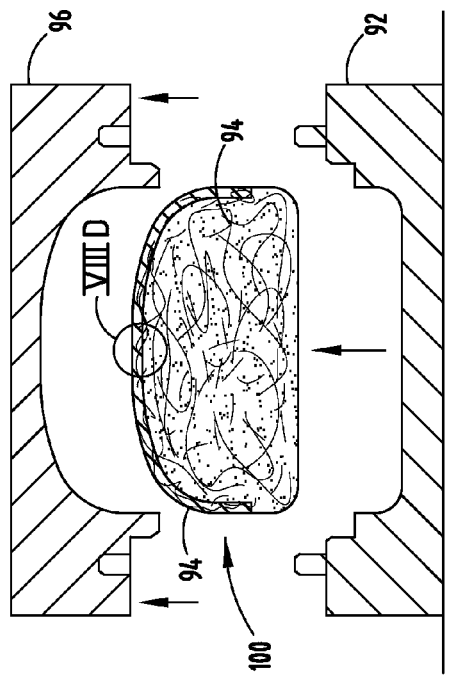
FIG. 8D is an enlarged view of the area VIIID of FIG. 8C.

Referring now to the embodiment illustrated in FIG. 5A, the soluble polymer (step 80) is combined with a liquid (step 36) and an aggregate (step 34) to form a liquid aggregate (step 81) including a solution of polymer particles. The concentration of polymer particles in the solution will vary depending on the amount of liquid versus the amount of soluble polymer used. In the case of a water soluble plastic film, the film can be broken-down in to smaller parts or pulverized to decrease the dissolving time. The resulting solution of polymer particles generally has the viscosity of water. Thus, the solution is suitable for injection molding procedures. The solution of polymer particles is then combined with a fungal inoculum (step 38) to form a slurry (step 82). The resulting mixture can then be placed in an enclosure such as an open mold or closed mold (step 83). The enclosure can then be placed in an environment suitable for growing the mycelium (step 84). As the hyphae grow (step 84), they will grow through and around the nutrients of the aggregate and the polymer particles, forming bonds with the particles which will remain in the final plasticized structure. Specifically, as the mycelium and plastic mixture grows, the chitin of the mycelium bonds with the soluble plastic polymer particles so as to fully and evenly incorporate the polymer particles into the resulting structure. The mixture of particles, mycelium and aggregate can also be injection or compression molded, sprayed onto a substrate by a spraying mechanism or placed into a suitable receptacle to form a sheet of material where it can grow and then be further processed by known means. The final structure will retain properties of the polymer such as the polymer's rigidity and strength. After the mixture has sufficiently grown (step 84), the part is cured (step 86) to end the growing cycle and then later formed (step 88) to the desired shape by known means as discussed below. The structure may be cured simply by allowing the plasticizer to harden which can effectively terminate mycelium growth. The resulting structure has significant rigidity due to the plastic polymer incorporated into the structure and varying amounts of polymer can be used in its creation to alter the properties of the structure. This allows for the finished composite part to be a thin-walled structure that does not require the density or size that a similar part would need to achieve a like rigidity. As the mycelium and water soluble plastic are biodegradable, the resulting part formed from the mycelium and plastic mixture is a rigid, durable and biodegradable part.

Referring now to FIGS. 7 and 8A-9A, another method of making a formed part includes providing an aggregate (step 34) and mixing the aggregate with a fluid (step 36) to create a liquid aggregate (step 32). A fungal inoculum is provided (step 38) and mixed with the liquid aggregate (step 39) to create a mixed slurry 90. The slurry 90 is placed into a mold cavity 92 (step 93) and a coverstock 94 is placed over the mold cavity 92 (step 95), as disclosed above in similar processes. It is contemplated that a top mold 96 may be placed over the mold cavity 92 (FIG. 8A), wherein the top mold 96 holds the coverstock 94 in place over the mold cavity 92 during cellular growth of the fungal inoculum into live mycelium 95. As shown in FIG. 8B, the mycelium 95 is allowed to grow over a predetermined length of time until the mycelium has physically engaged with an underside of the coverstock 94 (step 96). It is contemplated that the coverstock 94 may include an engagement side 98 having apertures or a porous surface area that aids the physical bond between the mycelium 95 and the coverstock 94. A vast array of interconnected hyphae of the live mycelium 95 literally grows into the engagement side 98, thereby physically coupling or connecting with the coverstock 94. As a result of the physical connection between the mycelium 95 and the coverstock 94, an adhesive is not required. Accordingly, a manufacturing step is eliminated. Other constructions that create an extended surface area on the engagement side 98 of the coverstock 94 for the mycelium 95 to latch onto are also contemplated. After the mycelium 95 has grown into secure connection with the engagement side 98 of the coverstock 94, heat is applied to the mold cavity 92 to terminate further growth of the mycelium 95 (step 99). The finished part 100 is then removed from the mold cavity 92 and is ready for further finishing (step 102) or installation into a vehicle (FIGS. 9 and 9A). In another embodiment, it is contemplated that the coverstock 94 may be heat-welded to the mycelium 95 or stretched over the mycelium 95.

Figure 10:
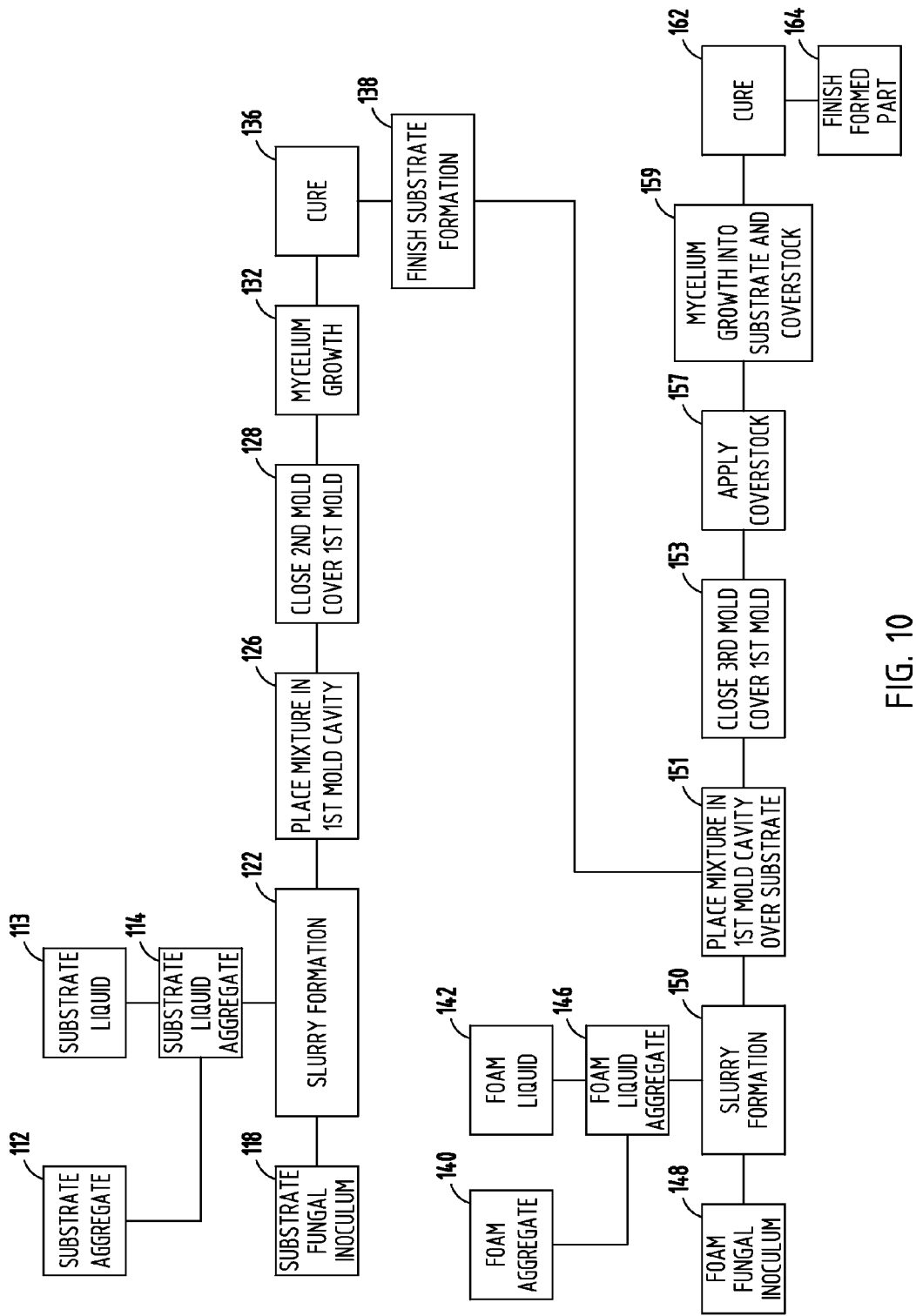
FIG. 10 is a flow chart illustrating one embodiment of a method of making a dual mycelium component.
Figure 11:
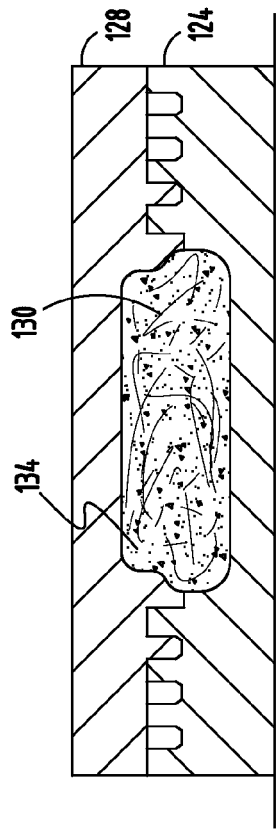
FIG. 11 is a side elevational cross-sectional view of a molding device for making a dual layer mycelium component.
Figure 11A:
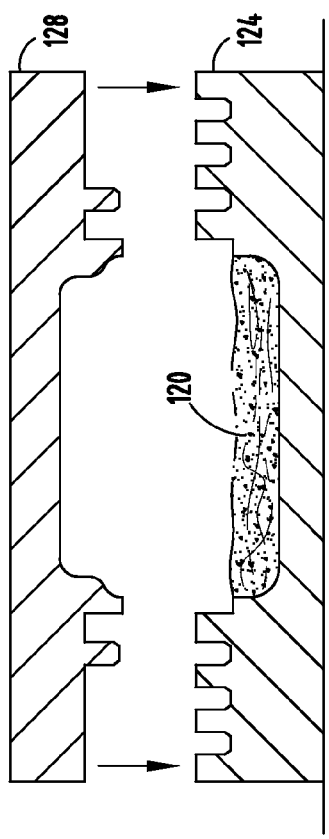
FIG. 11A is a side elevational cross-sectional view of the molding device of FIG. 11 shown in the closed position.
Figure 11B:
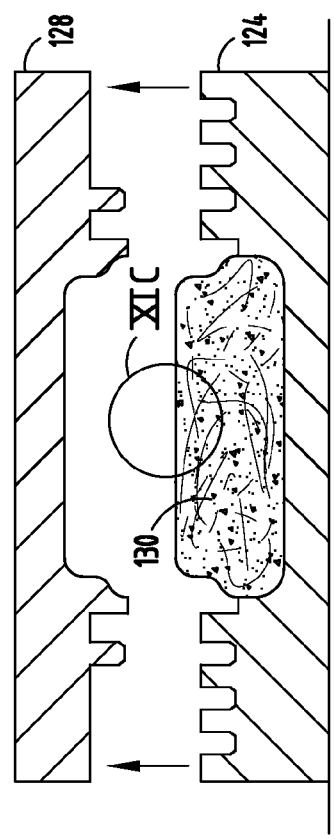
FIG. 11B is a side elevational cross-sectional view of the molding device of FIG. 11A shown in the open position.
Figure 11C:
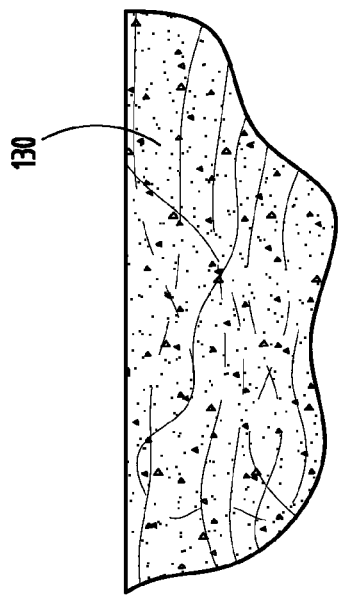
FIG. 11C is an enlarged view of the area XIC of FIG. 11B.
Figure 11D:
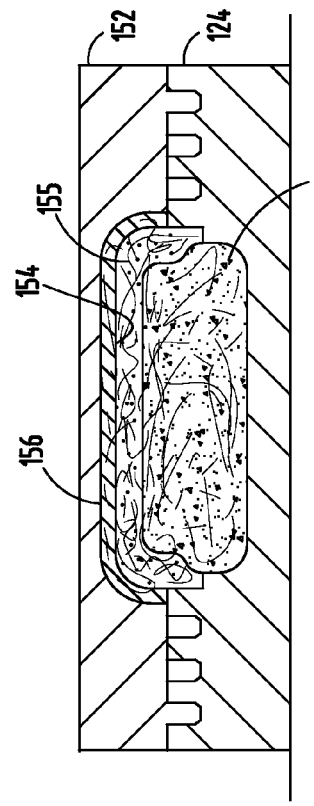
FIG. 11D is a side elevational cross-sectional view of the first mold component and third mold component of the molding device creating the dual mycelium component.
Figure 11E:
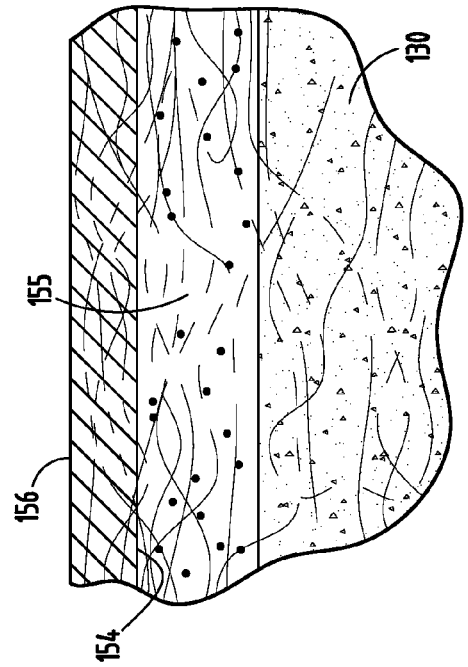
FIG. 11E is a side elevational cross-sectional view of the first and third mold components of the molding device of FIG. 11D in the closed position.
Figure 11F:
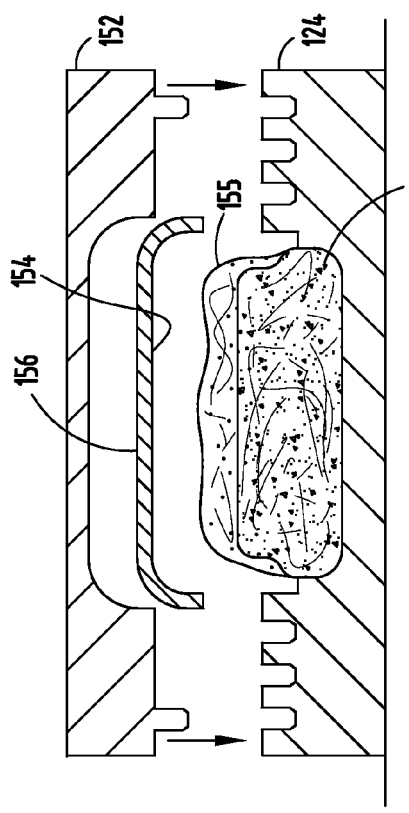
FIG. 11F is a side elevational cross-sectional view of the first and third mold components of the molding device of FIG. 11D in the open position.
Figure 11G:
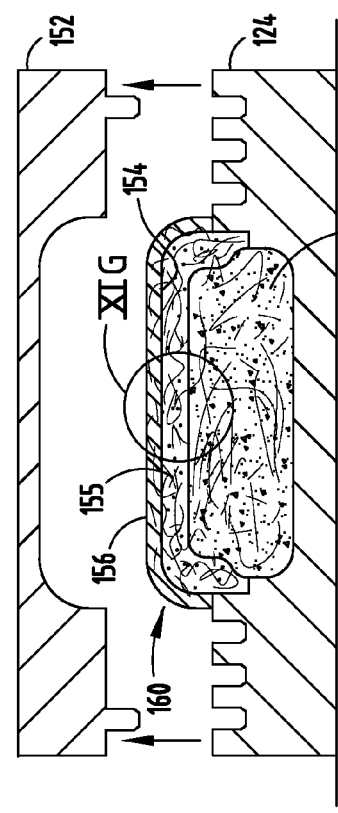
FIG. 11G is an enlarged view of area XIG of FIG. 11F.

Referring now to FIGS. 10 and 11-11G, another embodiment of making a formed part includes preparing an aggregate (step 112) and a fluid (step 113) that are particularly suited for making a high density structural component and mixing the aggregate with a liquid (step 114). The resulting liquid aggregate (step 114) that is formed is mixed with a fungal inoculum (step 118) to form a slurry 120 (step 122) designed to create a dense, rigid, and structurally sound substrate. The slurry 120 is then placed into a first mold cavity 124 (step 126). A second mold cavity 128 is closed over the first mold cavity 124 (step 128) and the fungal inoculum is allowed to grow into a mycelium substrate 130 (step 132). The humidity level is generally maintained at a level between 20 and 100 percent during growth of the mycelium. In addition, the temperature is maintained between 55 degrees Fahrenheit and 90 degrees Fahrenheit. After the mycelium substrate 130 has completely filled a void cavity 134 formed by the first and second mold cavities 124, 128, the mycelium substrate 130 is cured, such as by applying heat (step 136) to a temperature of 150 degrees Fahrenheit for a period of one to 15 days, to terminate further growth of the mycelium. After the mycelium substrate 130 is cured, the mycelium substrate 130 formation is complete (step 138).

Referring again to FIGS. 10 and 11-11G, at the same time or after the mycelium substrate 130 formation is occurring, an aggregate (step 140) and a liquid (step 142) that are specifically adapted for making a foam-like resilient mycelium structure are mixed to form a liquid aggregate (step 146). A fungal inoculum is introduced (step 148) that is designed for creating a foam-like final mycelium product and mixed with the liquid aggregate to form a slurry 149 (step 150). The second mold cavity 128 is removed from the first mold cavity 124 over the finished mycelium substrate 130. The slurry 149 is placed into the first mold cavity 124 over the mycelium substrate 130 (step 151). A third mold cavity 152 is then closed over the first mold cavity 124 (step 153) and the fungal inoculum adapted to make foam-like mycelium 155 is allowed to grow. A finished composite part 160 is formed and the part 160 is cured by heat or other means (step 162), as discussed above in previous embodiments. In the illustrated embodiment, the foam grows into an engagement side 154 of a coverstock 156 that is applied over the mycelium 155 (step 157) until the void between the third mold cavity 152 and the mycelium substrate 130 is completely filled by the growing foam-like mycelium 155 (step 159). The third mold cavity 152 is then removed and the finished part 160 is removed from the first mold cavity 124 for further finishing and trim work (step 164) or placement in a vehicle, such as that shown in FIG. 2. A dual mycelium component formed by this process is illustrated in FIGS. 12 and 12A.

Figure 13:
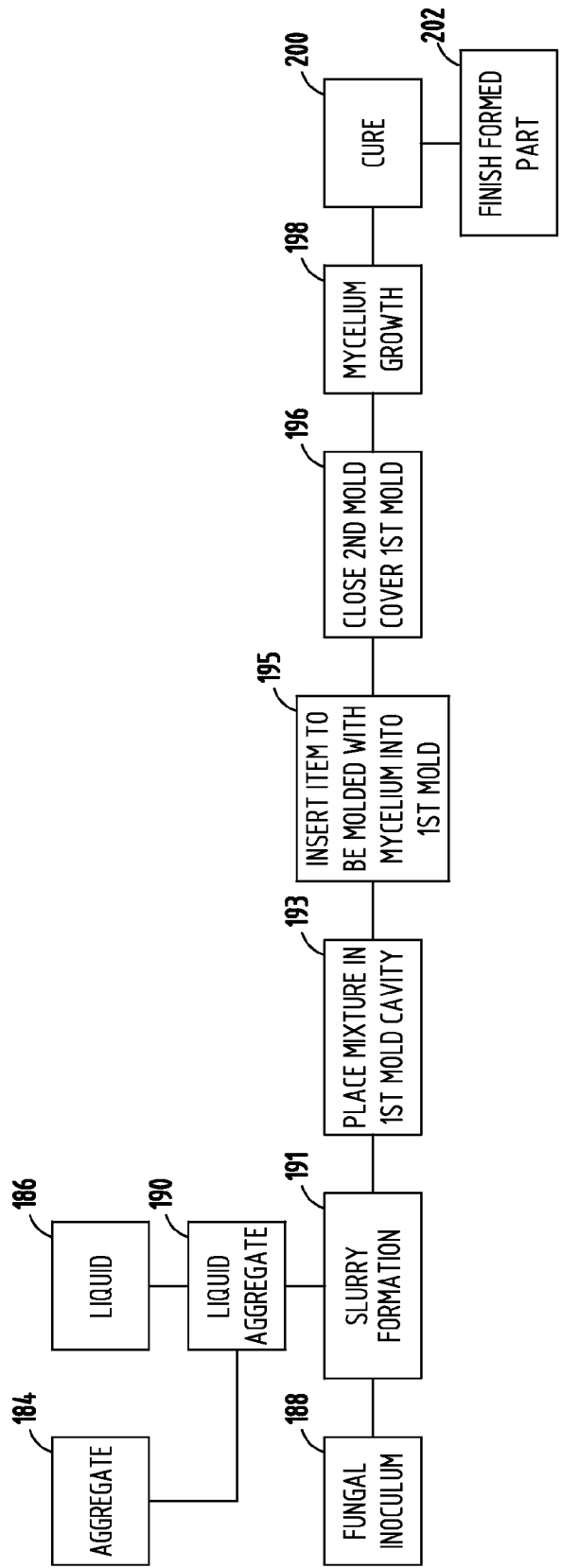
FIG. 13 is a flow chart illustrating one embodiment of a method of making a mycelium component with an object disposed therein.

Referring now to FIGS. 13 and 14-14C, in another embodiment, an object, such as a pin 180, as shown, or a hinge, fastener, etc., is placed into a mold 182 during growth of the mycelium. An aggregate is introduced (step 184) and a fluid is introduced (step 186) to form a liquid aggregate (step 190), and subsequently, a fungal inoculum (step 188) is added to the liquid aggregate and mixed to form a slurry (step 191). The slurry is placed into a first mold cavity 192 (step 193). At the same time, the pin 180 that is to be molded into the live mycelium is also inserted into the first mold cavity 192 (step 195). A second mold cavity 194 is closed over the first mold cavity 192 (step 196) and mycelium growth occurs (step 198), such that the mycelium hyphae grow into and bond with the item that is placed into the mold 182. After the mycelium growth has completely filled the mold cavity formed between the first and second mold cavities 192, 194, the mycelium is cured (step 200) to terminate further mycelium growth and a finished part 201 is removed (step 202). The part 201 may then be further processed or installed into a vehicle, such as that shown in FIG. 2.

Referring now to FIGS. 15-15B, a hardened tubular structure 220 is made by preparing an aggregate (step 222) and preparing a liquid (step 224) and mixing the aggregate with the liquid to create a liquid aggregate (step 226). A fungal inoculum is introduced (step 228) and mixed with the liquid aggregate to form a slurry (step 230). The slurry is placed into a mold cavity (step 232) and mycelium is allowed to grow (step 234) into a predetermined form. After the mycelium has grown into the predetermined form, the live mycelium is rolled into a tube-like structure (step 236) while still in the growth cycle forming multiple layers of mycelium (FIG. 15A). The mycelium is allowed to further grow into a tube-like form (step 238) with the hyphae extending from the mycelium, becoming interwoven in the center of the cylinder or tube. It is contemplated that the tube could have a diameter as large as three feet or as small as 0.125 inches. After the tube has been cured by heating or other means (step 239), a tubular finished part 240 is formed (step 242) and prepared for installation in a vehicle. The tubular finished part 240 includes a structure having different densities on an outside exterior portion 244 of the tube and an interior portion 246 of the tubular finished part 240. During growth of the live mycelium mat, the mycelium mat is rolled to form a lap joint 248 between the interior portion 246 of the tubular finished part 240 and the exterior portion 244 of the tube. It is contemplated that the lap joint 248 will be maintained as the hyphae on the interior portion 246 of the tubular finished part 240 grow and intertwine.

In another embodiment, as shown in FIG. 15B, a tubular finished part 250 is rolled several times prior to curing to create an interior portion 252 of the tubular finished part 250 with mixed densities throughout. As the tubular finished parts 240, 250 grow, the hyphae intertwine and fuse, creating a strong bone-like structure that, after curing, are used as structural supports in a variety of applications. The tubular finished part 250 may be rolled several times to form a larger tubular structure before a lap joint 254 is formed. Once again, it will be understood that the hyphae grow into one another in this rolled form until the curing process, at which time the tubular finished part 250 formed by the rolled mycelium is heated to a temperature greater than 150 degrees Fahrenheit to form a hardened tubular structure component.

The mycelium mat will generally be grown to a thickness of between approximately 0.125 inches and 2.0 inches, according to one embodiment. It is contemplated that the mycelium mat will be grown for at least one to 15 days, and it is also contemplated that an oxygen rich gas supply may be given to the mycelium mat to stimulate growth. The aggregate may be formed from any of the aggregates mentioned above, but it is contemplated that an aggregate formed from coconut, rice, corn, or a mixture thereof may be ideal in creating the mycelium mat, in particular, a mycelium mat having long intertwining hyphae.

The tubular structure will be cured by heating the tubular structure to the temperature of at least 150 degrees Fahrenheit for a period of at least one day. In addition, it is contemplated that moisture may be added to the tubular structure for a predetermined length of time to aid in rolling in forming the mycelium structure prior to the curing process. Subsequently, when the tubular structure is cured, much or most of the moisture is removed from the rolled mycelium mat to form the hardened tubular finished parts 240, 250. The hardened tubular finished parts 240, 250 are generally rods formed from mycelium.

In another embodiment, the hardened structure formed by this process is not rolled, but rather layered to form a substantially rigid structure having relatively flat sides. Any number of shapes can be made with the pliable living mycelium mat during the growth cycle. However, the shape should be formed during the mycelium growth so that the hyphae weave during the growth cycle, providing a strong unified core. As a result, after curing of the hardened elongate structure, much of the strength of the hardened elongate structure can be obtained by the interwoven hyphae in the center of the hardened elongate structure.

Figure 16:
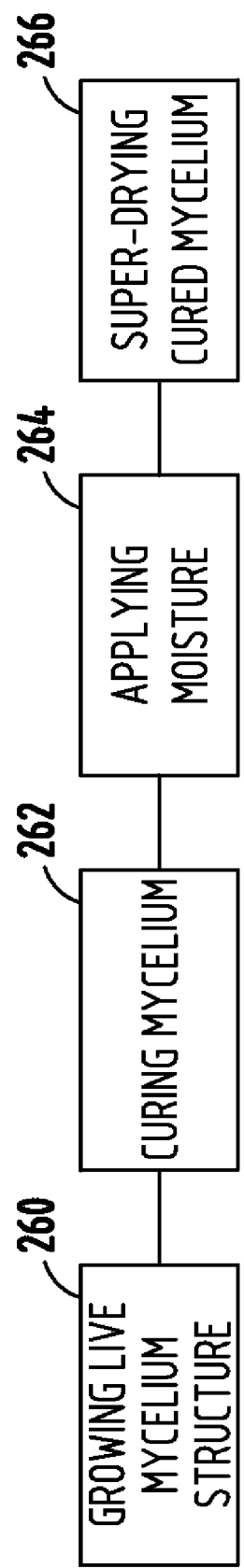
FIG. 16 is a flow chart illustrating an embodiment of a method of making a hardened mycelium component.
Figure 17A:
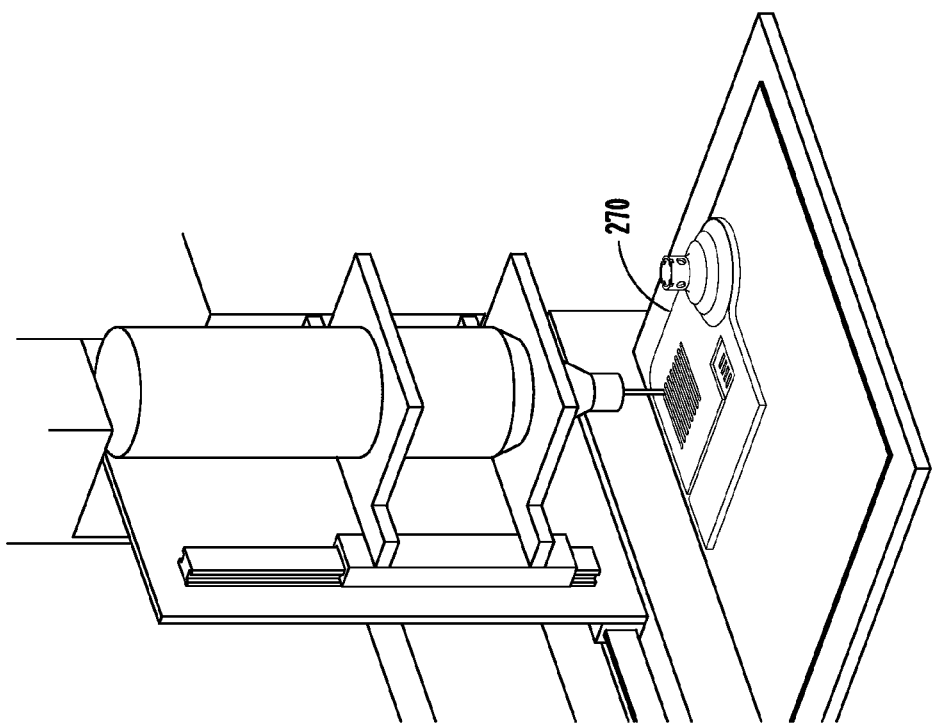
FIG. 17A is a top perspective view of one embodiment of the mycelium mat after cutting into a mycelium component.
Figure 17:
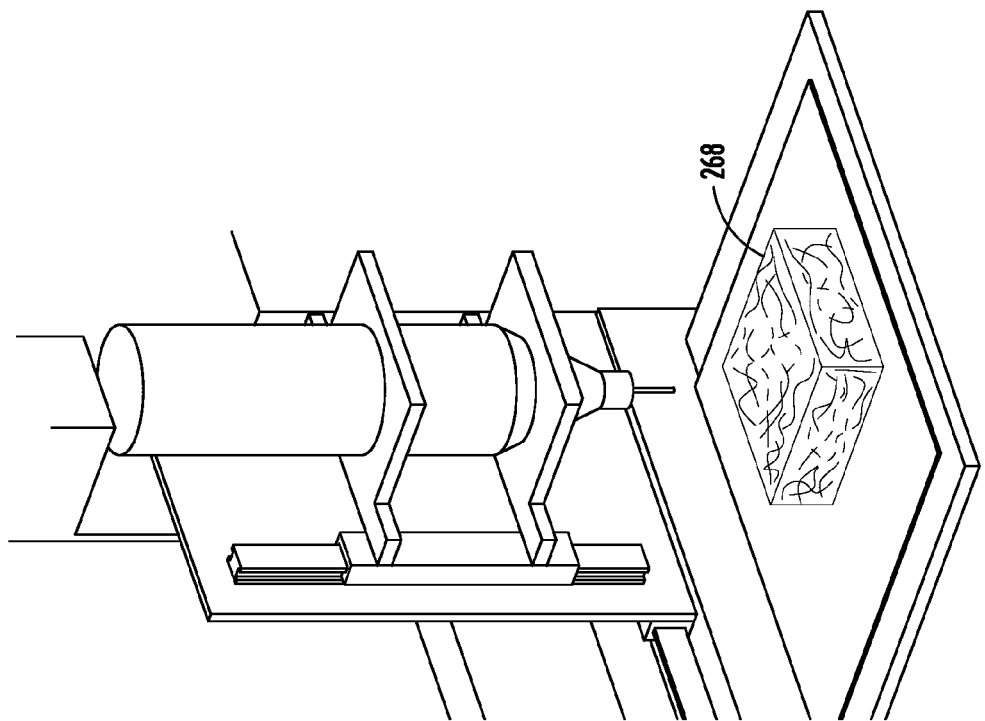
FIG. 17 is a top perspective view of one embodiment of a mycelium component prior to cutting.

Referring now to FIG. 16, it is also contemplated that the mycelium mat grown (step 260) in any of the several methods described above may be placed in a super-drying device. For example, the elongate part mentioned above could be placed in the super-drying device, which dry heats the rolled mycelium mat into the hardened tubular structure. The mycelium mat is then cured (step 262). The mycelium mat may then be moistened (step 264) to any saturation level, including 100 percent saturation, or super-dried directly (step 266). Super-drying the tubular structure causes increased rigidity and strength in the mycelium mat during the curing process. The super-drying device converts lignin that has not been digested by the mycelium during curing from a thermoplastic condition to a thermoset condition which substantially rigidifies the product. It is also contemplated that the curing process may be eliminated completely when the super-drying process is used to harden the tubular structure. The cured mycelium mat may be super-dried by dehumidification, kiln-drying, or any other procedure for removing moisture, strengthening, and hardening the subject material. The super-drying process lasts for at least one day in which the mycelium mat is subjected to temperatures of at least 150 degrees Fahrenheit. The super-dried mycelium mat achieves a greater hardness as a result of a low moisture content of between 5 and 25 percent. In another embodiment, the moisture content is lowered to less than one percent.

After the tubular structure has been super-dried, formed, and hardened, the tubular structure may be used in any of a variety of applications, including in a vehicle as a load supporting member. The tubular structure may also be used in construction, manufacturing, or any of a variety of other industries.

Referring now to FIGS. 17-19A, another method of making a vehicle part includes growing a live mycelium mat 268 by one of the processes described above and cutting the mycelium mat 268. The mycelium mat 268 is cured to terminate mycelium growth. The mycelium mat 268 is then cut into a single structural part 270 for use in a vehicle. The actual shape and size of the mycelium mat is determined based on the desired dimensions of the final cut part 270. It is contemplated that several structural parts 270 may be developed from one large mycelium mat 268.

The mycelium mat 268 may be any of a number of shapes and sizes in height, width, and depth, but is intended to be of a size that can be readily cut by standard cutting machines in the manufacturing industry. The single structural part may be cut using a laser cutter, water cutter, CNC machine, etc. In addition, it is contemplated that after the mycelium mat 268 has been cut into a single structural part 270, the part 270 may be covered with a laminate to maintain its shape, as well as maintain the moisture percentage of the single structural part 270.

To achieve a cuttable mycelium mat 268, a finely ground aggregate will generally be used. Although any of the aggregates listed above may be appropriate, it is generally contemplated that the aggregate will be a finely ground aggregate from the group consisting of coconut, rice, corn, cotton, and by-products thereof. In addition; it is contemplated that the mycelium mat 268 will be grown for at least one day and possibly as many as 15 days. An oxygen rich gas may be supplied to the mycelium mat during the growth cycle to facilitate faster growth and thicker development. In addition, to cure the mycelium mat, the mycelium mat will be heated to a temperature of at least 150 degrees Fahrenheit for one day.

Figure 18:
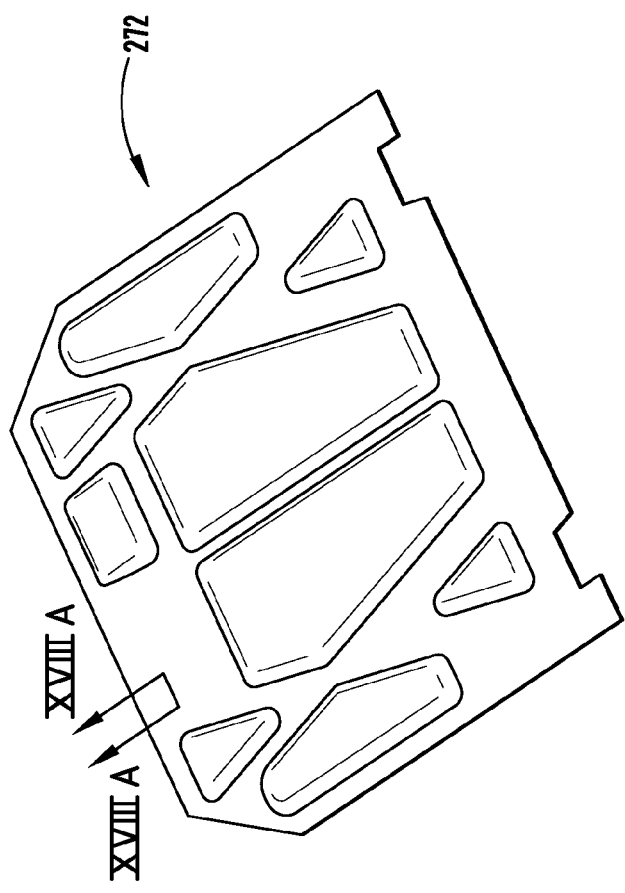
FIG. 18 is a top perspective view of one embodiment of the heat shield XVIII of FIG. 2 incorporating a mycelium component.
Figure 18A:
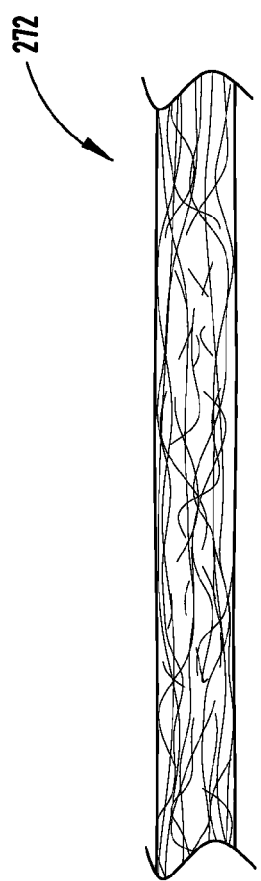
FIG. 18A is a cross-sectional view taken at line XVIIIA-XVIIIA.

Moisture may be applied to the mycelium mat on one or several occasions for a predetermined length of time. Subsequently, the mycelium mat will be heated to remove substantially all of the moisture gained during the application of moisture. Parts such as the heat shield 272 (FIGS. 18 and 18A) and the headliner part (FIGS. 19 and 19A) can be made by cutting the mycelium mat, as disclosed above.

The mycelium and aggregate slurry discussed above may also be treated with a foaming agent or foaming device that is capable of introducing a gas to the mycelium slurry which facilitates the growth of the hyphae network. Oxygen rich environments are ideal for hyphae development as fungus cells exchange gases directly with their atmosphere. Unlike photosynthetic plants, fungi breathe in oxygen and release carbon dioxide.

Figure 20:
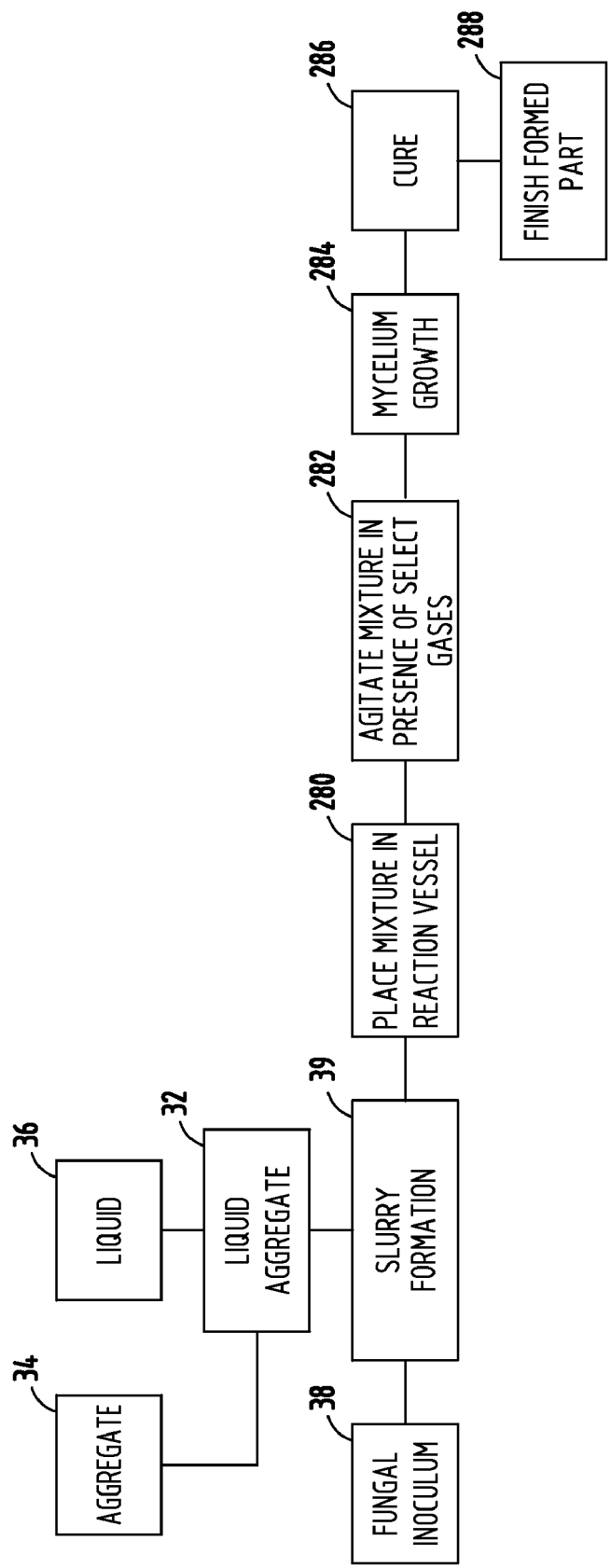
FIG. 20 is a flow chart illustrating one embodiment of a method of making a foamed mycelium component.

Referring now to FIGS. 20-22, a foamed mycelium product is made by placing the slurry of mycelium into a reaction vessel 290 (step 280). The reaction vessel 290 may be a foam production chamber known in the art, according to one embodiment, but other known reaction vessels will work, according to other embodiments. Typically, the reaction vessel 290 is generally in the form of a foam production chamber (FIGS. 21-22) having an agitation device 292, which is used to introduce a select gas into a mycelium slurry 294. The agitation device 292 can be a blending mechanism (FIG. 21), an external pump for direct injection of a gas into the reaction vessel 290 (FIG. 22), a controlled flow device to stir the slurry, or any other such agitation device known in the art for introducing a gas to a medium (step 282). As noted above, oxygen rich environments promote the growth of mycelium, so oxygen enriched gases are a good source of oxygen to use. Pure or free oxygen-containing gases such as air may also be used. Pure oxygen gases may also be diluted with inert materials such as nitrogen and carbon dioxide and other such gases to control the growth. The gases can be introduced under pressure as through an external pump, but may also be introduced by moderate to aggressive agitation of the slurry (step 282). Gases can also be introduced through a blowing agent, an effervescent substrate, or any other foaming process known in the art.

As shown in FIG. 20, the reaction vessel 290 includes an agitation device 292, which, in this embodiment, is a stirring mechanism. As the agitation device 292 agitates or stirs the slurry 294 (step 282), gases, indicated by lines A and B, are introduced to the slurry 294 through gas portals 296, 298. As the slurry 294 circulates, indicated by arrows E, the gases A and B become incorporated with the slurry 294 in the form of bubbles 300. The gases A and B can be the same or different gases, but typically produce bubbles 300 containing free oxygen that the slurry 294 will envelope and use for mycelium growth (step 284). As shown, the reaction vessel 290 may further include chambers 302 that help agitate the slurry 294 as it circulates and increase gas introduction. After the mycelium is allowed to begin its growth cycle, an optional second agitation step may occur further promoting gas bubble incorporation into the slurry and thereby further promoting mycelium growth. The mycelium component is then cured (step 286) and the part is finished (step 288) for insertion into a vehicle.

As shown in FIG. 22, the reaction vessel 290 can include an agitation device 292 in the form of an external pump. The pump introduces pressurized gas, indicated by lines F and G, into the slurry 294, such that bubbles 300 form in the slurry 294, creating a foaming effect. Gases, indicated by lines C and D, can also be introduced to the slurry 294 through gas portals 296, 298. As the slurry 294 grows into mycelium in the presence of the bubbles 300, a lightweight and less dense mycelium composite develops. The oxygen in the gases promotes the mycelium growth and hyphae interconnection as the hyphae will grow into the bubbles 300, forming bonds with adjacent hyphae. The promoted hyphae growth results in a composite with enhanced rigidity, which is also lightweight due to the foaming process which creates cavities formed by the bubbles 300 of gas which are incorporated in the final structure. Specifically, the resulting foam structure can be up to 50 percent lighter than a similar foamed structure produced using standard urethane techniques. Also, the resulting foamed structure is generally at least five percent lighter than a similar structure made from mycelium that is not foamed.

The various mycelium components discussed above, and the methods for making those components, provide strong parts adapted for use, in vehicles, both in aesthetic and structural capacities. The introduction of mycelium creates a biodegradable part that eliminates the need for adhesive in several instances, and reduces costs by eliminating manufacturing steps. The mycelium components can be grown into various shapes and sizes and include varying densities, depending on the aggregate used, the temperature during the growth cycle, and the total growth duration.

It will be understood that any of the processes or steps within those processes may be combined with other disclosed processes or steps to form structures within the scope of the present invention. The exemplary structures and processes disclosed herein are for illustrative purposes and are not to be construed as limiting.

It is to be understood that variations and modifications can be made on the aforementioned structures and methods without departing from the concepts of the present invention, and further it is to be understood that such concepts are intended to be covered by the following claims unless these claims by their language expressly state otherwise.

What is claimed is:

1. A method of making a mycelium structure, comprising:
    dissolving a soluble plastic film having insoluble polymer particles in a liquid to form a solution of polymer particles;
    combining the solution of polymer particles with a fungal inoculum and a nutrient source for the inoculum to form a mixture;
    growing a live mycelium network that bonds with the polymer particles to form a plasticized structure; and
    terminating growth.

2. The method of claim 1, wherein the step of combining the solution of polymer particles with a fungal inoculum further comprises:
    a fungal inoculum selected from the group consisting of *Pleurotus djamor, Pleurotus eryngii, Pleurotus ostreatus, Pleurotus ostreatus* var, *columbines, Grifola frondosa, Ganoderma lucidum, Ganoderma oregonense, Lentinula edodes, Agrocybe aegerita*, or Coprinus Comatus.

3. The method of claim 1, wherein the step of combining the solution of polymer particles with a fungal inoculum and a nutrient source further comprises:
    providing a nutrient source including a fibrous material from a plant to feed the fungal inoculum.

4. The method of claim 3, wherein the step of providing a nutrient source including a fibrous material from a plant further comprises:
    providing a fibrous material selected from the group consisting of coconut, rice, corn, and cotton.

5. The method of claim 1, wherein the step of combining the solution of polymer particles with a fungal inoculum and a nutrient source further comprises:
    providing a nutrient source having lignin.

6. The method of claim 1, wherein the step of terminating growth further comprises:

heating the structure to a sufficient temperature for a sufficient period of time to terminate growth.

7. The method of claim 6, wherein the step of heating the structure to a sufficient temperature for a sufficient period of time to terminate growth further comprises:

heating the structure to a temperature of at least 150 degrees Fahrenheit for at least one day.

8. A vehicle part comprising:
a body portion
comprising the mycelium structure produced by the method of claim 1.

* * * * *